(12) United States Patent
Ullah et al.

(10) Patent No.: US 11,596,623 B2
(45) Date of Patent: Mar. 7, 2023

(54) METHODS FOR TREATING VIRUS INFECTION OR PROLIFERATION

(71) Applicants: HOWARD UNIVERSITY, Washington, DC (US); GEORGETOWN UNIVERSITY, Washington, DC (US)

(72) Inventors: Hemayet Ullah, Washington, DC (US); Sivanesan Dakshanamurthy, Herndon, VA (US)

(73) Assignees: HOWARD UNIVERSITY, Washington, DC (US); GEORGETOWN UNIVERSITY, Washington, DC (US)

( * ) Notice: Subject to any disclaimer, the term of this patent is extended or adjusted under 35 U.S.C. 154(b) by 0 days.

(21) Appl. No.: 17/289,558

(22) PCT Filed: Oct. 29, 2019

(86) PCT No.: PCT/US2019/058544
§ 371 (c)(1),
(2) Date: Apr. 28, 2021

(87) PCT Pub. No.: WO2020/092354
PCT Pub. Date: May 7, 2020

(65) Prior Publication Data
US 2022/0096442 A1 Mar. 31, 2022

Related U.S. Application Data

(60) Provisional application No. 62/752,018, filed on Oct. 29, 2018.

(51) Int. Cl.
*A61K 31/4196* (2006.01)
(52) U.S. Cl.
CPC ................. *A61K 31/4196* (2013.01)
(58) Field of Classification Search
CPC ........................ C07D 249/12; A61K 31/4196
See application file for complete search history.

(56) References Cited

U.S. PATENT DOCUMENTS 5,776,716 A 7/1998 Ron et al.

FOREIGN PATENT DOCUMENTS

WO 2008/157407 A2 12/2008
WO 2017/165885 A1 9/2017

OTHER PUBLICATIONS

Hemayet Ullah et al. "Host targeted antiviral (HTA): functional inhibitor compounds of scaffold protein RACK1 inhibit herpes simplex virus proliferation," Oncotarget, May 14, 2019 (May 14, 2019), pp. 3209-3226, vol. 10, No. 35.
Jakob Nilsson et al. "Regulation of eukaryotic translation by the RACK1 protein: a platform for signalling molecules on the ribosome," EMBO Reports, Dec. 1, 2004 (Dec. 1, 2004), pp. 1137-1141, vol. 5, No. 12.
Simone Gallo et al. "RACK1 Specifically Regulates Translation through Its Binding to Ribosomes," Molecular and Cellular Biology, Dec. 2018, pp. 1-16, vol. 38, Issue 23.
International Search Report of PCT/US2019/058544 dated Feb. 4, 2020 [PCT/ISA/210].
Written Opinion of PCT/US2019/058544 dated Feb. 4, 2020 [PCT/ISA/237].

*Primary Examiner* — Kamal A Saeed
(74) *Attorney, Agent, or Firm* — Sughrue Mion, PLLC

(57) ABSTRACT

A method for treating against, or at least inhibiting or suppressing, the proliferation of an internal ribosome entry site-utilizing virus (IRES-utilizing virus) involves administering a compound, a tautomer, or a pharmaceutically acceptable salt thereof, in an amount effective for inhibiting replication of the IRES-utilizing virus in cells, wherein the compound is represented by the formula:

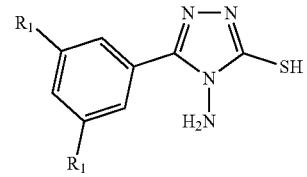

wherein each $R_1$ is independent of the other and represents a halogen atom selected from the group consisting of bromo, chloro, fluoro and iodo.

11 Claims, 19 Drawing Sheets
Specification includes a Sequence Listing.

A

B

C

SEQUENCE LISTING

<160> NUMBER OF SEQ ID NOS: 7

<210> SEQ ID NO 1
<211> LENGTH: 17
<212> TYPE: DNA
<213> ORGANISM: Artificial Sequence
<220> FEATURE:
<223> OTHER INFORMATION: Synthetic sequence, primer for HSV-1 ICP0 - forward

<400> SEQUENCE: 1
ctgcgctgcg acacctt                                                17

<210> SEQ ID NO 2

```
<211> LENGTH: 22
<212> TYPE: DNA
<213> ORGANISM: Artificial Sequence
<220> FEATURE:
<223> OTHER INFORMATION: Synthetic sequence, primer for HSV-1
      ICP0 - reverse

<400> SEQUENCE: 2
caattgcatc caggttttca tg                                              22

<210> SEQ ID NO 3
<211> LENGTH: 21
<212> TYPE: DNA
<213> ORGANISM: Artificial Sequence
<220> FEATURE:
<223> OTHER INFORMATION: Synthetic sequence, primer for
      beta-actin - forward

<400> SEQUENCE: 3
ggttccgatg ccctgaggct c                                               21

<210> SEQ ID NO 4
<211> LENGTH: 21
<212> TYPE: DNA
<213> ORGANISM: Artificial Sequence
<220> FEATURE:
<223> OTHER INFORMATION: Synthetic sequence, primer for
      beta-actin - reverse

<400> SEQUENCE: 4
acttgcggtg cacgatggag g                                               21

<210> SEQ ID NO 5
<211> LENGTH: 28
<212> TYPE: DNA
<213> ORGANISM: Artificial Sequence
<220> FEATURE:
<223> OTHER INFORMATION: Synthetic sequence, primer sequence for HIV
      gag - forward

<400> SEQUENCE: 5
ataatccacc tatcccagta ggagaaat                                        28

<210> SEQ ID NO 6
<211> LENGTH: 25
<212> TYPE: DNA
<213> ORGANISM: Artificial Sequence
<220> FEATURE:
<223> OTHER INFORMATION: Synthetic sequence, primer sequence for HIV
      gag - reverse

<400> SEQUENCE: 6
ttggtcctgt ctatgtccag aatgc                                           25

<210> SEQ ID NO 7
<211> LENGTH: 674
<212> TYPE: DNA
<213> ORGANISM: Homo sapiens

<400> SEQUENCE: 7
caccccaagg gcccacgtgg cggctagtac tctggtattt cggtaccttt gtacgcctgt     60
tttatctccc ttcccaatgt aacttagaag ctctcaaatc aaagctcaat aggtggagcg    120
caaaccagcg ctctcacgag caagcactcc tgtctccccg gtgtggttgt ataaactgtc    180
cccacggttg aaaacaacct atccgttatc cgctatagta cttcgagaaa cctagtatca    240
```

-continued

```
cctttggatt gttgatgcgt tgcgctcagc acactaaccc gtgtgtagct tgggtcgatg    300
agtctggaca tacccactg gcgacagtgg tccaggctgc gttggcggcc tactcatggt    360
gaaaaccatg agacgctaga catgaacagg gtgtgaagag tctattgagc tactatagag   420
tcctccggcc cctgaatgcg gctaatctta accatggagc aagtgctcac aagccagtga   480
gttgcttgtc gtaatgcgca agtccgtggc ggaaccgact actttgggtg tccgtgtttc   540 acttttact tttatgactg cttatggtga caatttgata ttgttaccat ttagcttgtc    600
aaatcaatta caaaagaccc taaatcttat ttatcaactt gcattttgat aactttaatt   660
tgaaaatttt gata                                                     674
```

METHODS FOR TREATING VIRUS INFECTION OR PROLIFERATION

CROSS-REFERENCE TO RELATED APPLICATIONS

This application claims priority from U.S. Application No. 62,752,018, filed Oct. 29, 2018, the disclosure of which is incorporated herein in its entirety by reference.

BACKGROUND

It has been reported that various viruses use a host's RACK1 (Receptor for activated C kinase 1) protein to translate viral mRNA using a viral mRNA secondary structure known as the Internal Ribosomal Entry Site (IRES). Cell, 159(5):1086-1095 (2014). For example, Enteroviruses include viruses such as EV-D68, which replicate in a host by using the viral Internal Ribosomal Entry Site (IRES) structure. Focused Reviews, Annals ATS, 12(5): 775-781 (2015); Science, 347(6217):71-74 (2015).

Enteroviruses ("EV") can infect humans and include EV-71, such as EV-71A; EV-B, such as Coxsackievirus B3 (CVB3); EV-C, such as Polioviruses (PV-1, PV-2, PV-3); EV-D, such as Enterovirus D68 (EV68, EV-D68, HEV68), RV-A, such as human rhinovirus 16 (HRV16); RV-10 (HRV14), and RV-C.

Enterovirus D68 (EV-D68) is a member of the Picornaviridae family. Since its first isolation in 1962, and although once considered rare, EV-D68 has been on a worldwide upswing in the 21st century. While some uncertainty may exist, it has been implicated in cases of a polio-like disorder called acute flaccid myelitis.

A relatively recent outbreak of this Enterovirus resulted in thousands of patients being hospitalized and deaths of at least 11 children in the United States. There are apparently no known approved cures for such a viral infection in cells, e.g., in a patient, Buontempo et al., Antimicrobial Agents and Chemotherapy, 41(6):1220 (1997); Germann et al., Focused Reviews, Annals ATS, 12(5):775 (2015).

Enterovirus D68 (EV-D68) was reported as a causative agent in outbreaks in the U.S. of respiratory illness in children. Science, 347(6217):71-74 (2015).

In past decades, Enterovirus EV-71 has been the etiological agent in large scale epidemics. It has been reported that there are no currently approved vaccines or antiviral therapies for the treatment and prevention of EV-71 infections. Shang et al., Antiviral Res., 97(2):183-94 (February 2013).

In fall 2018 an outbreak of polio-like symptoms in patients has been reported. The malady is called acute flaccid myelitis (AFM). The affected patients are for the most part young. Reports are that about 90% of the patients are 18 or younger. Although potential causes are under investigation, in an initial press report Enterovirus EV-D68 has been singled out as one of the potential culprits for causing the AFM outbreak.

SUMMARY

Example embodiments of the disclosed subject matter herein provide methods for treating an infection or proliferation of an internal ribosome entry site (IRES)-utilizing virus in a host.

In addition, example embodiments of the disclosed subject matter herein provide compounds effective in treating a host in need of treatment against such viruses, such as an Enterovirus.

Example embodiments of the disclosed subject matter herein also provide methods for at least inhibiting or suppressing host RACK1 protein; and methods for treating, or at least inhibiting or suppressing, IRES-dependent viral translation. The methods include treating, or at least inhibiting or suppressing, viral infection from an IRES-dependent virus in a host comprising administering an effective amount of a compound, a tautomer, or a pharmaceutically acceptable salt thereof, to the cell(s) for interfering with the interaction of a host's RACK1 protein with at least a portion of the virus genome containing a sequence for the viral Internal Ribosome Entry Site (IRES). The compound(s), tautomer(s) or pharmaceutically acceptable salts are believed to target the functional sites of the host's RACK1 protein. It is believed the treatment increases instability of such protein and can lead to depletion of RACK1 in the ribosome. This stops, or at least inhibits or suppresses, viral replication (proliferation or propagation) in infected cells by interfering with the IRES-dependent translation of viral mRNA (e.g., non-capped viral RNA).

In one of its aspects, such a method of treating, or at least inhibiting or suppressing, a viral infection from an IRES-utilizing virus comprises administering a therapeutically effective amount of a compound, a tautomer thereof or a pharmaceutically acceptable salt for interfering with replication of the viral mRNA, in which the compound is represented by the formula (1):

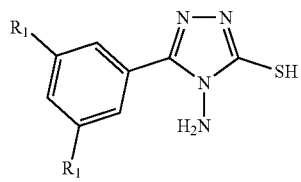

in a host in need of treatment. Each $R_1$ represents, independent of the other, a halogen atom at the meta positions on the phenyl ring. The method of treating involves interfering with, or at least inhibiting or suppressing, viral mRNA replication in the infected cells thereby stopping, or at least inhibiting or suppressing, viral proliferation.

DETAILED DESCRIPTION

Figure 1A:
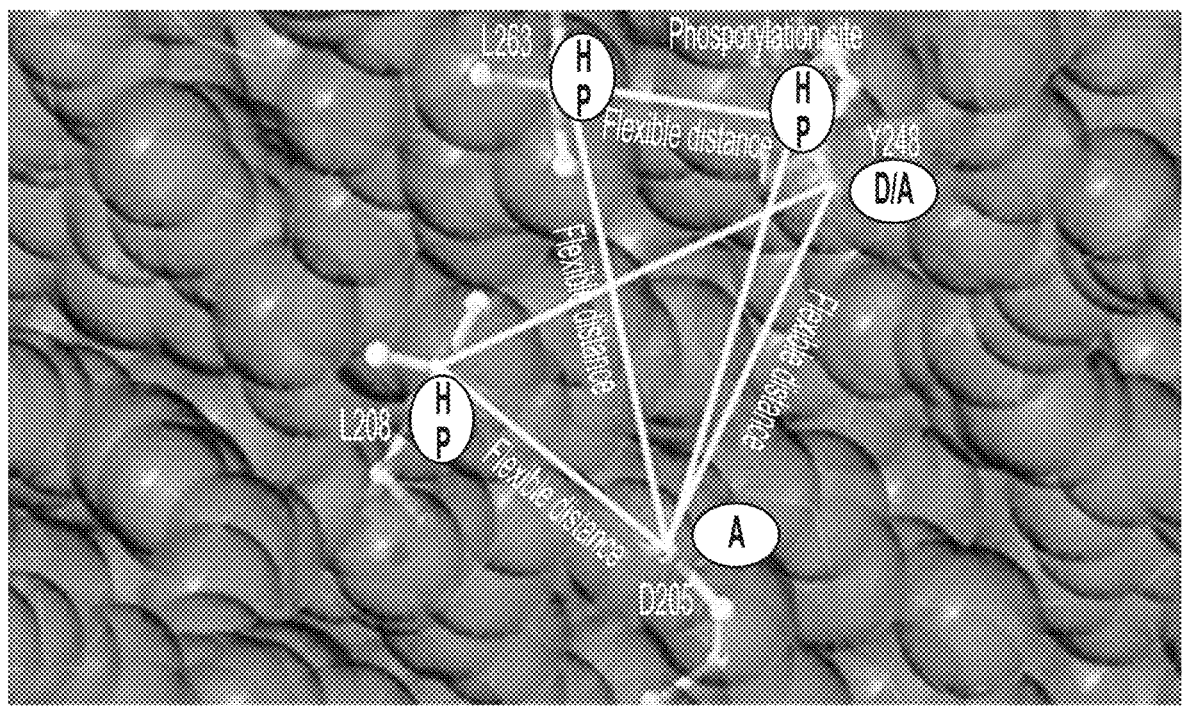
FIG. 1A shows sample two receptor-based three-point pharmacophore models generated on the RACK1A phosphorylation site with exclusion spheres colored pink, geometric and distance constraints (flexible) shown as lines, and filled white circles as centers. HPhydrophobic; D-donor; A-acceptor.
Figure 1B:
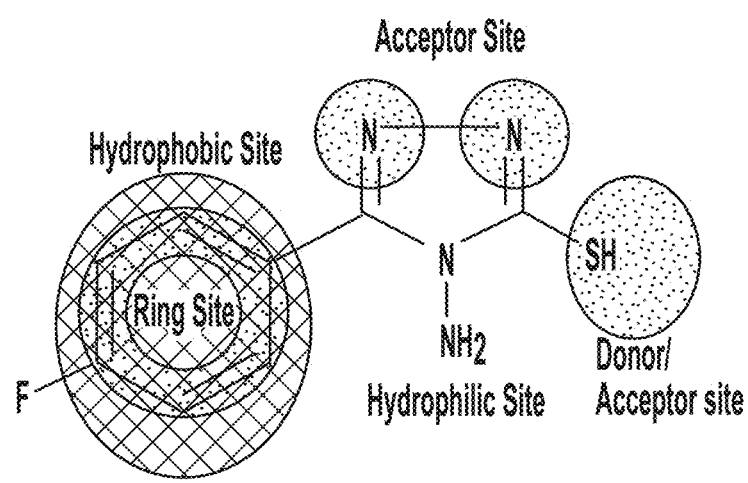
FIG. 1B shows ligand-based pharmacophore model generated on SD-29 with pharmacophore constraints acceptor, donor, hydrophobic ring, and hydrophilic sites represented by filled circles. Structures of compounds SD-29-12 and SD-29-14 are shown.
Figure 1B:
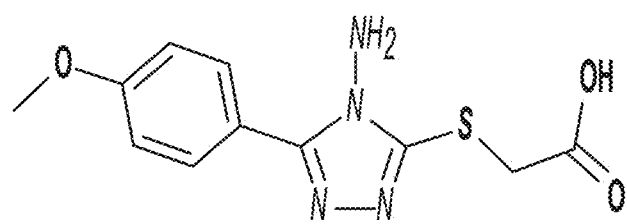
Figure 1B:
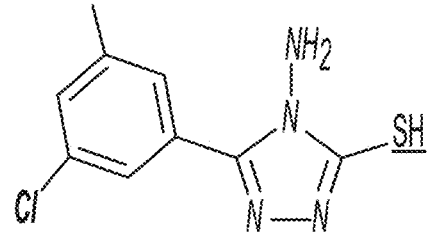

A method for treating, or at least inhibiting or suppressing, an IRES-utilizing virus in a host comprises administering a therapeutically effective amount of a compound, or a tautomer thereof or a pharmaceutically accept salt thereof, capable of inhibiting or interfering with viral proliferation. An internal ribosome entry site (IRES)-containing virus refers to a virus requiring a host's receptor for Activated C Kinase 1 (RACK1) protein to interact with the viral IRES for viral mRNA translation. RACK1 is a specific host factor required for IRES-mediated translation by such viruses, such as HCV. Thus, without being restricted thereto, it is believed the compound(s), its tautomer(s), or its pharmaceutical salts interfere with the host's RACK1 thereby blocking its interaction with the viral mRNA of an IRES-utilizing virus required for IRES-dependent viral replication.

A method for treating, or at least inhibiting or suppressing, such a virus comprises treating a host infected with such virus with an amount of one or more compounds, tautomers thereof, or pharmaceutically acceptable salts thereof, effective for interfering with replication of the internal ribosome entry site utilizing virus (IRES-utilizing virus) in the host. The treating involves administering the compound(s), its tautomer(s), and/or its pharmaceutical salts to the host. The compound is represented by the formula (1):

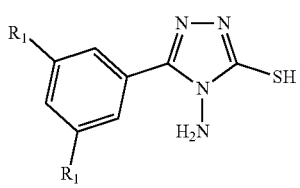

Formula (1)

wherein each $R_1$ is independent of the other and each represents a halogen atom.

Accordingly, in an aspect of a method for treating, inhibiting or suppressing an IRES-utilizing virus, each $R_1$ independent of the other represents a halogen atom selected from the group consisting of bromo, chloro, fluoro and iodo.

A compound represented by formula (2), which is an example of a compound represented by formula (1), a tautomer thereof, or a pharmaceutically acceptable salt thereof, is administered to a host in need of treatment to at least effect inhibition or suppression, if not block, replication of a IRES-utilizing virus:

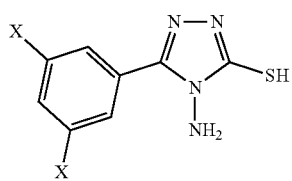

Formula (2)

wherein each X is the same and represents a halogen atom (bromo, chloro, fluoro, or iodo).

It will be appreciated that the administration can be to a host that is a patient in need of treatment or to cells.

A compound, denoted SD-29-14, its tautomer or a pharmaceutically acceptable salt is illustrative. This compound represented by formula (3) below:

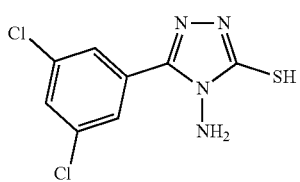

Formula (3)

The compounds of formula (1), (2) and (3) are capable of treating against, or at least inhibiting or suppressing, viral replication (proliferation) of an IRES-utilizing virus.

It is preferred that in a present method the compound exhibit comparatively lower relative cell toxicity while exhibiting effectiveness in treating against the IRES-utilizing virus.

One of the preferred compounds has chloro at the meta positions of the phenyl ring.

In above formulae (1), (2) and (3), by preference the azole moiety is shown with an —SH substituent and it will be appreciated tautomers in which there is a =S moiety instead may be used.

Pharmaceutically acceptable excipients and salts are described in Remington, The Science and Practice of Pharmacy, 20$^{th}$ Edition (2000). Salts are described at pages 703-711. A hydrohalide, such as a hydrochloride of a compound herein is an example.

Example embodiments of the disclosed subject matter herein provide a method for treatment that unexpectedly shows at least a marked impairment (inhibition/suppression) of viral replication of mRNA (e.g., non-capped mRNA) for IRES-utilizing viruses. Such IRES-utilizing viruses require a host ribosomal protein known as RACK1 for IRES-mediated translation (replication) of viral mRNA, and the disclosed methods herein provide a treatment that interferes with the host RACK1 protein to thereby block IRES-mediated translation of the viral mRNA in IRES-utilizing viruses.

A compound represented by a formulae herein functions as a RACK1 inhibitor. A related method therefor comprises administering an amount of a compound of a formula (1), (2) or (3), or a tautomer or a pharmaceutically acceptable salt thereof, in an amount effective for inhibiting a host's RACK1 protein. Sites targeted by the RACK1 inhibitor include such sites as the Y248 site (as in *Arabidopsis*) and/or similar sites in human RACK1 (e.g., Y246 site in human RACK1). In addition, other sites, such as the so-called K273 pocket and similar site(s) in human RACK1 might be another target sites. A RACK1 inhibitor interferes with the site(s) (sometimes called pocket(s)) in the RACK1 of interest, such as human RACK 1, so that the RACK1 as modified by a compound of a formulae herein is inhibited. Inhibited RACK1 in a host involves disrupting the interaction of the host RACK1 with the viral IRES required for IRES-mediated translation of viral mRNA (e.g., uncapped viral with poly A tail).

A compound represented by a formula herein exhibits an improvement in stopping, or at least inhibiting or suppressing or stalling, viral replication of an IRES-utilizing virus which involves disrupting the interaction of a host RACK1 protein with the viral IRES required for IRES-mediated translation of viral mRNA (e.g., uncapped viral mRNA).

A compound represented by a formula herein exhibits an improvement in inhibiting viral replication of an IRES-utilizing virus as compared to a compound (SD-29) in which the phenyl ring is mono-substituted (fluoro) at the para-position.

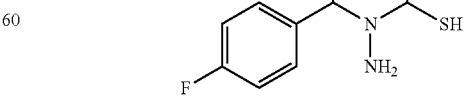

Data show the efficacy using the SD-29-14 compound for treating against viral IRES-mediated translation as in an IRES-utilizing virus, such as HSV-1, starts in vitro at a lower concentration, such as at 1 µM (which is 100 times better than that of a SD-29 compound), and in a dose dependent way, and is effective in at least inhibiting, suppressing or stalling HSV-I proliferation. This is supported, for example, from data obtained from using a Luciferase signal as the measurement of HSV-I proliferation as the virus is tagged with the luciferase signal producing tag.

A compound represented by a formula herein exhibits an improvement in inhibiting viral replication of an IRES-utilizing virus as compared to a compound known as SD-29-12.

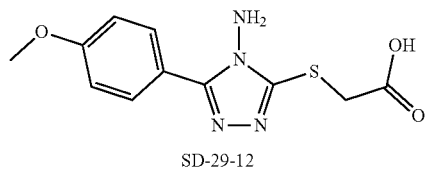 [SMILES: COc1ccc(-c2nnc(SCC(=O)O)n2N)cc1]

SD-29-12

Diverse viruses utilize a host protein, known as Receptor for Activated Kinase 1 (RACK1) to translate mRNAs using a secondary structure known as the Internal Ribosome Entry Site (IRES). In other words, RACK1 plays an essential role in the IRES-dependent translation of the mRNA of such viruses. In a method using a compound described herein the compound can target and bind to the RACK1 functional site(s) in the host's RACK1 to produce modified RACK1, such as to increase instability of the RACK1 protein. In principle, depletion of modified RACK1 from the host cell (as supported by data from Western assay(s)), can be the potential mechanism as without the RACK1 in the ribosome, IRES-containing viruses would not be able to replicate their mRNAs (e.g., non-capped mRNA).

Example embodiments of the disclosed subject matter herein provide a method for treating against IRES-utilizing pathogenic viruses.

Representative species of IRES-utilizing viruses have been identified via suitable software, such as the IRESPred software, as described in Kolekar et al., IRESPred: Web Server for Prediction of Cellular and Viral Internal Ribosome Entry Site (IRES), Scientific Reports, 6:27436 (June 2016). IRESPred reported IRES-containing viruses including HIV-1, Herpes Simplex Virus (HSV), and Hepatitis viruses to have IRES in their 5'UTR (Untranslated Region). Replication/proliferation of these IRES-utilizing viruses in a host via IRES-mediated translation of their viral mRNA can be inhibited by a present method.

IRES-containing viruses requiring IRES-dependent translation that can be treated against by a present method include viruses in the Flaviviridae family of viruses, viruses in the Picornaviridae family of viruses, viruses in the Poxvirus family of viruses, and viruses in the Herpesviridae family of viruses, by way of examples. The Flaviviridae family of viruses include Hepatitis C, Zika virus, West Nile Virus, and Dengue virus. IRES-containing viruses, such as Hepatitis C (HCV) and Dengue Virus NS1 require host RACK1 protein for IRES-mediated translation of virial mRNA. Cell, 159 (5):1086-1095 (2014) (Hepatitis C); Cell Reports, 21(13): 3900-3913 (Dec. 26, 2017) (Dengue Virus NS1). HCV is a positive strand RNA virus dependent on a highly structured IRES for its translation. The Picornaviridae family of viruses include the enteroviruses, such as Enterovirus D68 among others, apathoviruses, cardioviruses and hepatoviruses, among others. The Picornaviridae family of viruses is described in Current Pharmaceutical Design, 10:3757-3767 (2004). Enteroviruses, such as EV-D68, are described in AnnalsATS, 12(5):775-781 (2015); and Science, 347(6217): 71-74 (2017). The Poxvirus family of viruses include the Vaccina (Vac V) virus as an example. The Herpesviridae family of viruses includes Herpes Simplex Virus (e.g., HSV-1 and HSV-2).

Representative IRES-utilizing viruses include, for example, HSV-1, HIV-1, EV-D68 and Hepatitis C virus (HCV).

Data show that a compound(s) described herein disrupts or interferes with a host RACK1 protein (e.g., in yielding modified RACK1). Data show such compound(s) can be administered to at least inhibit proliferation/replication of IRES-dependent viruses. RACK1 mediated translation is a critical step in virus propagation for IRES-dependent viruses. Impairing RACK1 can therefore lead to blocking or inhibiting or suppressing such IRES-utilizing viruses. Data from in vitro testing indicate the compound(s) are able to inhibit IRES activities in representative IRES-utilizing viruses, such as HCV, HSV-1 and EV-D68, by way of examples.

In a present method, a host is said to be in need of treatment. The host may comprise cells in a mammal (patient, e.g., human) in need of treatment. It will also be appreciated that the method can be practiced with cells in vivo or in vitro.

Compounds in accordance with a formula herein can be prepared by adapting the following synthesis.

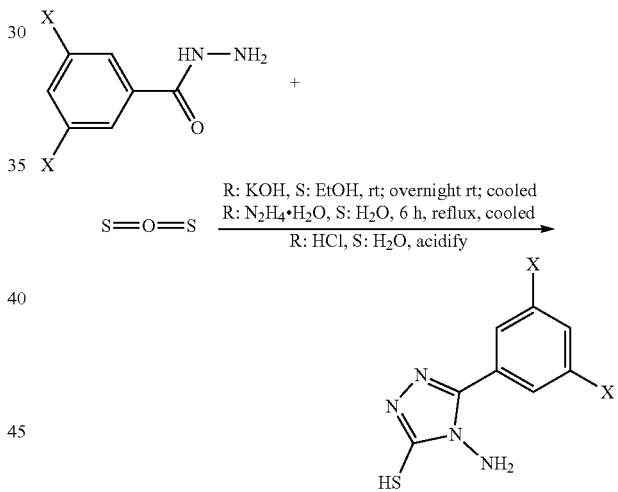

Each X, independent of the other, represents a halogen atom.

An exemplary method for synthesizing a compound known as SD-29-14 is:

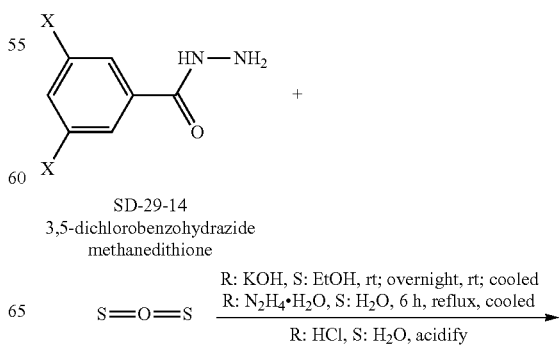

SD-29-14
3,5-dichlorobenzohydrazide
methanedithione

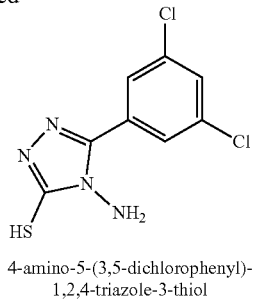

4-amino-5-(3,5-dichlorophenyl)-
1,2,4-triazole-3-thiol

Other syntheses can be adapted from Molecules, 6:815-824 (2001).

Compounds of a formula, such as formulas (1)-(3), can also be synthesized by adapting the following synthesis. The hydrazide (0.04 mol) and KOH (0.04 mol) in 50 cm$^3$ MeOH is treated with CS2(0.04 mol), and the mixture is stirred for 16 hr at room temperature. Diethyl ether (50 cm$^3$) is added, and the precipitated solid is filtered, washed with ether, and vacuum-dried at 78° C. in a drying pestle. The potassium salts of substituted dithiocarbazinic acids are used for the next step without further purification. The potassium salt of the substituted dithiocarbazinic acid (0.02 mol) and hydrazine hydrate (0.04 mol) in 2.0 cm$^3$ water are heated under reflux with stirring for 0.5-1.5 h. The color of the reaction mixture changes to green with the evolution of hydrogen sulfide, and a homogeneous solution is formed in about a half an hour. When evolution of hydrogen sulfide ceases (lead acetate test), the reaction mixture is diluted with 50 cm$^3$ cold water and acidified with 6 N hydrochloric acid. The precipitated solid was filtered, washed with cold water, and recrystallized from aqueous EtOH.

A general discussion of determining the effect of inhibition of IRES-mediated translation appears in Plank et al., Nucleic Acids Research 41(13):6698-6714 (2013).

The expression of a protein within the viral genome can be assessed by diverse means. For example, the tagged protein may exhibit luminescence or fluorescence so as to permit the amount of expression to be determined by the amount of light given off by the culture and/or a lysate thereof. In combination or the alternative, the expression of a protein may be determined by the binding of various markers, such as antibodies, for proteins within the viral genome. Other means known to those skilled in the art of detecting the presence or absence of a protein within a viral genome following infection of cell culture may also be used. Regardless of the manner in which expression of protein within a viral genome is assessed, diminished amounts of the assessed protein in infected cultures treated with a compound in accordance with any of the formulae herein, or a pharmaceutically acceptable salt thereof, compared to identically infected cultures not treated with the compound or its salt evidences the capacity of the compound and/or its salt to inhibit expression of at least a portion of a virus genome containing an IRES sequence.

Assessing the expression of an introduced protein may enable an assessment of viral proliferation by means not normally permitted by the native viral genome. For example, proliferation of an IRES-containing virus treated (e.g., inhibited or suppressed) by a present method, can be assessed using luminescence. Accordingly, proliferation of a luminescence-modified virus will entail production of the luciferase protein. As the luciferase protein causes fireflies to glow, production of the luciferase protein by infected cells as a result of viral proliferation will enable infected cells actively proliferating the luminescence-modified virus to glow. However, if cells infected with the IRES-containing virus modified for luminescence do not glow when administered a compound in accordance with a formulae herein, or a pharmaceutically acceptable salt thereof, or a tautomer thereof, then the compound, its tautomer, or its salt is capable of inhibiting expression of at least a portion of the viral genome containing an IRES sequence. Inhibiting expression of at least a portion of the viral genome means the compound would inhibit proliferation of the virus.

Figure 5:
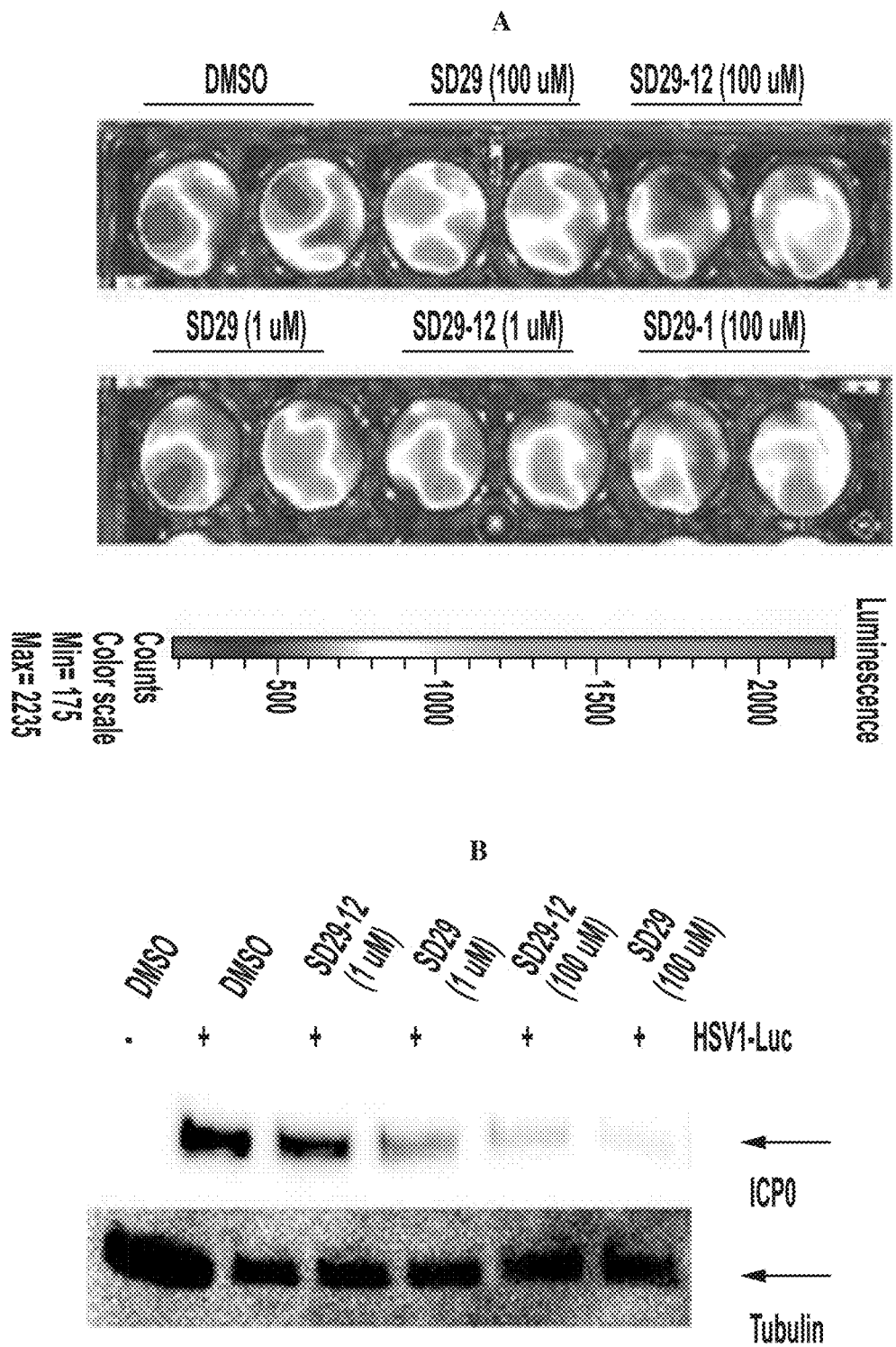
FIG. 5 shows that co-treatment of drugs with virus increases efficacy. Panel A of FIG. 3 shows the effect of drugs at the indicated concentrations after 24-hour post-infection with HSV1-Luc (4×106 pfu/ml media), and the same treatments are shown in duplicates. Panel B of FIG. 5 depicts a result of assaying HSV-1 major structural protein ICP0 expression from the 48-hour post infection samples as shown in FIG. 5(A). The expression of tubulin was used as loading control (lower panel).

Visualization of the RACK1 inhibitor induced inhibition of IRES-containing viruses is illustrated with HSV-1 proliferation in the HEp-2 cells. As an IRES-containing virus an HSV-1 F strain expressing luciferase (R84I 1 mutant) under the control of the ICP27 promoter was used. HEp-2 cells were grown to 80-90% confluency in Dulbecco's Modified Eagle's medium (DMEM) supplemented with 10% fetal calf serum (PCS) and 1% penicillin-streptomycin (PS) and fungicide. The HSV-1 virus and a concentration of an inhibitor compound(s) of a formulae herein were added and incubated for 24 h and for 48 h (FIG. 5). The luciferase signals were imaged and quantified in a Perkin Elmer IVIS Spectrum Imaging system. A. The inhibitor compound(s) effectively inhibited the HSV-1 proliferation as can be seen in a dose dependent reduction in the luciferase signal.

Or, stated differently, visualization of the RACK1 inhibitor induced inhibition of IRES-containing viruses is illustrated by the following protocol. To 80-90% confluent HEp-2 cells, HSV-1-Luc (R8411) are added at a concentration of 2×10e$^6$ pfu/ml along with indicated concentration of inhibitor compounds. After the described incubation period, luciferase activity is evaluated from bioluminescence images acquired by a Perkin Elmer IVIS Spectrum Imaging system immediately after adding luciferase substrate (D-luciferin, Gold Bio Technology) at a concentration of 400 μg/mL in medium. Bioluminescence intensity in different wells is quantified in units of photons per second per centimetre squared per steradian (p/s/cm$^2$/sr) by drawing a polygonal region of interest over the signals in images using Living Image 3.0 software (Caliper Life Sciences).

RACK1 regulates IRES-mediated translation in transformed HEp2 cells with IRES plasmids as indicated by dual-luceriferase reporter constructs. Dual-luciferase reporter constructs can be used to determine if the drug targets IRES-mediated translation. Renilla luciferase (Rluc) translation is cap-dependent while the firefly luciferase (Fluc) translation depending on HIV-1/HCV IRES was utilized. The Fluc/Rluc ratio is measured in the presence or the absence of the compounds in HEp2 cells transfected with the dual-luciferase plasmid bearing either the wild-type (no IRES) or an IRES. As an example, HCV IRES was used as a positive control for IRES activities while Beta-globin sequence (No IRES) was used as a negative control. Dual-luciferase reporter constructs were generously adopted from (Plank, T. D., J. T. Whitehurst, and J. S. Kieft, Cell type specificity and structural determinants of IRES activity from the 5' leaders of different HIV-1 transcripts. Nucleic Acids Res, 2013. 41(13): p. 6698-714) and (Carvajal, F., et al., Structural domains within the HIV-1 mRNA and the ribosomal protein S25 influence cap-independent translation initiation. FEBS J, 2016. 283(13): p. 2508-27). The cells get transfected with the plasmids using Lipofectamine 3000 Reagent, from Thermo Fisher Scientific. Then treated with compounds SD-29, SD-29-12, and SD-29-1 at different concentrations; 1 μM and 100 μM. Moreover, the cells are treated with Dimethyl sulfoxide (DMSO) as a vehicle control or left untreated. SV40 promoter produces a capped and poly-adenylated dicistronic message. Translation of the upstream cistron (*renilla* luciferase, RLUC) is cap dependent, whereas translation of the downstream cistron (firefly luciferase, FLUC) occurs cap independently. IRES activity is measured by calculating the ratio of FLUC to RLUC light production (RLUs)(Plank et al., Nucleic Acids Research, 41(13):6698-6714 (2013). The results show equal cap-dependent translation coming from *renilla* while the absence of IRES-dependent translation coming from firefly signals in cells transformed with the beta-Globin plasmid. However, with HIV-1 gag ladder plasmid, a significant reduction in luciferase signals coming from firefly in cells that have been treated with RACK1 inhibitors. Moreover, the HCV IRES activities, arising from IRES activity inhibitor compounds are found to be significantly lower luciferase signals resulted from the firefly in cells that have been treated with RACK1 inhibitor compounds indicating that the inhibitor compounds are very specifically inhibiting both HIV-1 and HCV IRES activities. The control plasmids (beta-globin and defective EMCV IRES) showed signals coming mostly from cap-dependent translation of *renilla* luciferase and the ratio of Fluc to RLUC shows almost no IRES activities from these control constructs. This is consistent with compounds of a formulae herein inhibiting HIV-1 proliferation through inhibiting IRES-based viral translation.

Figure 3:
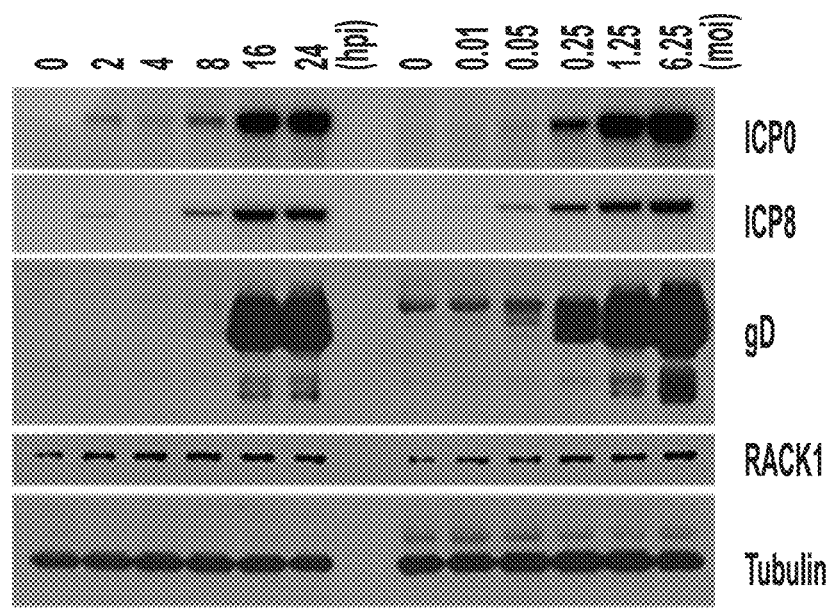
FIG. 3 shows effects of the compounds on HSV-1 protein expression. Panel A of FIG. 3 depicts time and concentration dependent virus protein expression to deduce an optimum drug treatment regimen. Left panel shows the time dependent HSV-1 virus protein expression after infection with HSV-1 17 at an MOI 1.25. Right panel shows the same virus protein expression under different concentrations of virus starting from 0.01 to 6.25 MOI. Panel B of FIG. 3 shows a result demonstrating that Hep-2 cells were pre-treated with the compounds for 24 h, and three different virus proteins (ICP0, ICP8, and gD) were assayed 24 h post infection with different titers of HSV-1. Red arrows show the downregulated virus proteins and blue arrow shows the downregulated RACK1 protein. Tubulin expression was used as the loading control for the blots.
Figure 3:
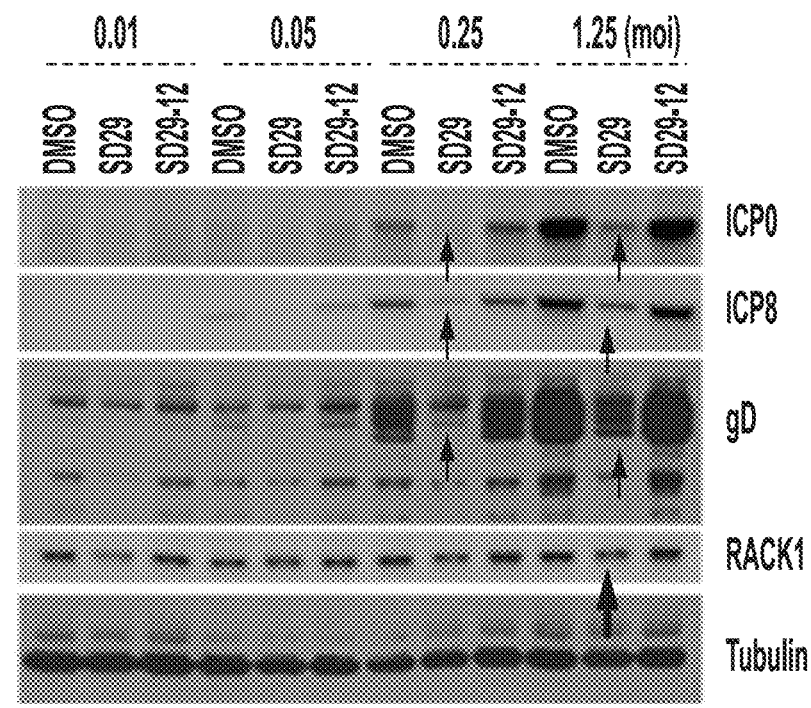

Another technique for indicating RACK1 inhibitor induced inhibition of IRES-utilizing viruses comprises the Western assay. As an IRES-utilizing virus, a virus representative of the Picornaviridae family of viruses (such as an Enterovirus, e.g., EV-D68) was evaluated via a Western assay, which indicated that a compound of the formulae, such as the di-chloro compound designated SD 29-14, inhibits proliferation of a representative virus (EV-D68), in a dose dependent way in a HEp-2 cell line. HEp-2 cells were grown to 80-90% confluency in Dulbecco's Modified Eagle's medium (DMEM) supplemented with 10% fetal calf serum FCS and 1% penicillin-streptomycin (PS) and fungicide. The representative virus (EV-D68) and the indicated concentration of compounds were added and incubated for 48 h. After washing with PBS, the cell lysates were collected and were run in a Biorad XT-Criterion gel and transferred to a PVDF membrane. The membrane was blotted with an antibody directed against the EV-D68 major structural protein VP1 purchased from Genetex (Irvine, Calif.). An anti-mouse IgG-HRP secondary antibody and Biorad's Western ECL substrate-Clarity was used to label the bands and the image was obtained in a Biorad Gel doc system. The cells treated with a representative compound (e.g., SD-29-I4) effectively inhibited the viral major structural protein VP1 (top panel with arrow in FIG. 3). The middle panel in FIG. 3 shows that the inhibition correlates with the loss of RACK1 protein in the same samples. The tubulin antibody was used as the loading control. Cells without any virus did not show any virus specific band but did show the RACK1 and tubulin expression. Reduction of major structural protein can potentially limit the virus ability to package itself into a fully formed infective virus.

Data for other IRES-utilizing viruses, such as the HSV-1 virus, obtained by using the above-described Western assay technique confirms in a present method the compound of a formula herein is effective in stopping, if not inhibiting or suppressing or stalling, viral IRES-mediated translation of viral mRNA.

That is, in a present method the compounds may be said to be broad anti-virals as they function as RACK1 inhibitors. A RACK1 inhibitor can therefore comprise a present compound, a tautomer thereof, or a pharmaceutically acceptable salt thereof, and can additionally include a carrier suitable for the selected method of administration. For example, the RACK1 inhibitor can be formulated in solid dosage form, such a capsule, tablet or the like, or can be formulated in a liquid suitable for administration orally or by injection.

Another technique for assessing inhibition of viral infection by a compound or its pharmaceutically acceptable salt is the broadly used and facile plaque assay technique. In general, in determining inhibition of viral replication the cytopathic effect in the form of plaque formation over time is assessed by comparing virus-infected cells treated with a vehicle such as DMSO against virus-infected cells treated with the compound, a tautomer thereof or a pharmaceutically acceptable salt thereof.

A virus proliferating using an Internal Ribosome Entry-Site (IRES) for viral mRNA translation may be referred to herein as an IRES-utilizing or IRES-containing virus. In other words, an internal ribosome entry site (IRES)-utilizing virus refers to a virus requiring a host's RACK1 protein to interact with the viral IRES for viral mRNA translation.

Based on the data, the compounds of formulae herein, such as the compound SD 29-14, and their tautomers and pharmaceutically acceptable salts, can interfere with (impair) a host's RACK1 protein by interfering with the functional site(s) of the RACK1 protein in a host and thus interfere with interaction between the functional RACK1 protein(s) of the host and the viral IRES so as to interfere with the viral IRES-mediated translation of viral mRNA translation thereby stopping, or at least inhibiting or suppressing or stalling, viral replication.

The complete disclosures of all patents and literature referenced herein and the disclosure of the Appendix hereto are incorporated herein by reference.

Detailed Description of Exemplary Embodiments

Hereinafter, the present application will be described in further detail with reference to examples. The examples are merely provided to more fully describe the present application, and it will be obvious to those of ordinary skill in the art that the scope of the present application is not limited to the following examples.

Example 1: Inhibition of HSV-1 Proliferation

1. Materials and Methods
Tissue Culture and Viruses
HEp-2 cells (ATCC) were used for the infection of HSV-1. The cells were maintained in Dulbecco's Modified Eagle's medium (DMEM) supplemented with 10% fetal calf serum (FCS) and 1% penicillin-streptomycin (PS). Wild-type HSV-1 17 was obtained from R. D. Everett and used previously Antibodies
The antibodies used for Western blot (WB) and immunofluorescence are listed below. A monoclonal antibody against tubulin (T-9026) was purchased from Sigma-Aldrich (St. Louis, Mo., USA; 1:1000 for WB); polyclonal antibody against ICP8, and monoclonal antibodies against HSV ICP0, ICP4, RACK1 and gD were purchased from Santa Cruz Biotechnology, Inc. (Santa Cruz, Calif., USA).

Purification of Viruses
Herpes viruses were amplified in Vero cells. The viral supernatant was centrifuged at 8000 g for 20 min to remove cell debris. The clarified medium was transferred into SW27/28 ultra-clear centrifuge tubes that were underlain with 7 mL of 20% sorbitol buffer (20% D-sorbitol, 50 mM Tris-HCl, pH 7.2, and 1 mM MgCl) and centrifuged at 55,000 g for 1 hour. The purified viral pellet was resuspended in PBS. The HSV-1 F strain expressing luciferase (R8411) under the control of the ICP27 promoter was a gift from Bernard Roizman (University of Chicago) and was constructed using an HSV-1 bacterial artificial chromosome (BAC) system described in Horsburgh et al. Horsburgh B C, Hubinette M M, Tufaro F. Genetic manipulation of herpes simplex virus using bacterial artificial chromosomes. Methods Enzymol. 1999; 306:337-52.

Bioluminescence Luciferase Assay

To 80-90% confluent HEp-2 cells, HSV1-Luc (R8411) was added at a concentration of $2\times10e^6$ pfu/ml along with indicated concentration of inhibitor compounds. After the described incubation period, luciferase activity was evaluated from bioluminescence images acquired by a Perkin Elmer IVIS Spectrum Imaging system immediately after adding luciferase substrate (D-luciferin, Gold Bio Technology) at a concentration of 400 µg/mL in medium. Bioluminescence intensity in different wells was quantified in units of photons per second per centimeter squared per steradian (p/s/cm²/sr) by drawing a polygonal region of interest over the signals in images using Living Image 3.0 software (Caliper Life Sciences).

Immunoblot Analysis

Proteins were separated by SDS-PAGE (25 µg loaded in each lane), transferred to nitrocellulose membranes (Amersham Inc., Piscataway, N.J., USA), and blocked with 5% nonfat milk for 60 min at room temperature. Membranes were incubated overnight at 4° C. with primary antibody, followed by incubation with a horseradish peroxidase-coupled secondary antibody and detection with enhanced chemiluminescence (Pierce, Rockford, Ill., USA), according to standard methods. Membranes were stripped with stripping buffer (100 mM 2-mercaptoethanol, 2% SDS, 62.5 mM Tris-HCl, pH 6.8), washed with PBS-0.1% Tween-20, and used to detect additional proteins. For *Arabidopsis* lysates one-week old seedlings were treated with 10 uM of ABA in the presence/absence of the inhibitor compounds for 12 hours in a growth chamber (overnight) at 22° C. mostly in the dark. Lysates were isolated in lysis buffer (Cell Signaling, Danvers, Mass.) supplemented with plant protease inhibitor (Sigma-Aldrich), phosphatase inhibitor cocktail A and B (Santa Cruz Biotechnology, Dallas, Tex.), and N-Ethylamaleimide (Sigma-Aldrich, St. Louis, Mo.). Twenty five microgram of proteins were loaded on the BioRad's 4-12% precast Bis-Tris polyacrylamide gel, transferred to a nitrocellulose membrane and then blocked with 5% Bovine Serum Albumin (BSA) for one hour, washed and incubated with the an antibody (1:100 dilution) to detect phosphorylated Y248 residue of RACK1A protein which was raised using the epitope: FSPNR{pTYR}WLCAATEH (Genscript, Piscataway, N.J., USA). To make it specific to RACK1A pY248, it was raised by adsorbing against the RACK1A non-phosphorylated antigen and to a peptide antigen with sequence FSPNRYWLCAATEN specific for the *Arabidopsis* RACK1B and RACK1C proteins. A rabbit secondary antibody (1:5000) was used. BIORAD's Clarity ECL substrate was used to visualize the bands. For loading control, the same membrane stripped in mild stripping buffer and then probed with an *Arabidopsis* Actin antibody (Sigma-Aldrich, St. Louis, Mo.) to show the loading control.

RNA Isolation and Real-Time RT-PCR

Following instructions of the manufacturers, total RNA was isolated using Tri Reagent® (Ambion, Inc., Austin, Tex.). To quantitatively examine the mRNA level of HSV-1 ICP0 from the infected cells, real-time RT-PCR was undertaken using the QuantiTect SYBR Green RT-PCR kit (QIAGEN, Valencia, Calif.). The primers for HSV-1 ICP0 were: forward-5'-CTGCGCTGCGACACCTT-3' (SEQ ID NO: 1) and reverse-5'-CAATTGCATCCAGGTTTTCATG-3' (SEQ ID NO: 2); and the primers for beta-actin (as control) were: forward-5'-GGTTCCGATGCCCTGAGGCTC-3' (SEQ ID NO: 3) and reverse-5'-ACTTGCGGTGCACGATGGAGG-3' (SEQ ID NO: 4). 1 µg of total RNA and 0.2 µM of sense and antisense primers (amplifying the RNA fragment in NS5 location) were used in a final 25 µl master mix volume. PCR reactions consisted of 50 cycles with the following optimal conditions: 94° C. for 20 s; 50° C. for 1 min; 72° C. for 30 s; and an optimized collection data step, 80° C. for 5 s. Fluorescence (captured at 80° C.) was determined to be absent from the signal generated by primer dimers. Data were collected and recorded by the BIORAD CFX Manager software. The relative quantity of the ICP0 transcripts at the indicated time points was normalized to the relative quantity of the reference gene actin at the same time points and then the $\log_{10}$ copy number of the normalized RNA transcripts were calculated and presented on a bar chart. A melting temperature curve analysis was obtained by measuring (after the amplification cycles) the fluorescence during a period of warming from 60° C. to 95° C.

Plaque Formation Unit (pfu) Assay

The viral plaque assay was performed as previously described [Tang Q, Li L, Ishov A M, Revol V, Epstein A L, Maul G G. Determination of minimum herpes simplex virus type 1 components necessary to localize transcriptionally active DNA to ND10. J Virol. 2003; 77:5821-28.] with slight modifications. The HSV-1 strain 17 was diluted serially in a volume of 1 mL. Then 300 ul of the virus was added onto confluent HEp-2 cell monolayers in 12-well plates; each dilution had 3 wells. After adsorption for 2 h, the medium was removed and the cells were washed twice with serum-free DMEM and overlaid with phenol-free DMEM containing 5% FCS, 0.5% low-melting point agarose (GIBCO), and 1% penicillin-streptomycin. The cells were incubated at 37° C. for 48 hours. Neutral red was added on the agarose to stain the live cells. The plaques were counted and reported as pfu per mL. Mean pfu was determined after averaging the number of pfu from different dilutions. Student's t-tests were used to statistically analyze differences between the groups; a p-value lower than 0.005 was used as the threshold for a significant difference.

Immunofluorescence and Confocal Microscopy

Hep-2 cells were grown to about 80% confluency in 12 well plate and the cells were co-infected with HSV-1 at an MOI of 1.0 for 30 h along with the indicated inhibitor compounds and control. The cells were fixed at room temperature with 4% paraformaldehyde-PBS for 15 minutes and then permeabilized at room temperature by 0.5% Triton X-100-PBS (pH 7.4) for 10 min. The cells were then washed 3× with Ice cold PBS. The cells were incubated with 1% BSA, 22.52 mg/mL glycine in PBST (PBS+0.1% Tween 20) for 30 min to block unspecific binding of the antibodies. The cells were incubated in the 1:500 diluted anti-ICP0 antibody in 1% BSA in PBST in a humidified chamber overnight at 4° C. The cells were washed three times in PBS, 5 min each wash and then incubated with the anti-mouse FITC conjugated secondary antibody in 1% BSA for 1 h at room temperature in the dark. After washing three times with PBST for 5 minutes each, the cells were mounted on slide using Prolong Slowfade Gold with DAPI (4=,6=-diamidino-2-phenylindole; Invitrogen), and confocal analysis was performed using Nikon CSU series Spinning Disk confocal microscope. Images were taken to show infected cells (green) and total viable cells (with DAPI stained nuclear DNA).

Fluorescence Cell Sort: Hep-2 cells were grown to about 80% confluency in T25 Cell culture flask and were co-infected with HSV-1 at a MOI of 1.0 for 24 h along with the indicated inhibitor compounds and control. After trypsinization, the cells were fixed in 4% paraformaldehyde-PBS. The cells were treated in the same method as described in the immunofluorescence and confocal microscopy method section. The labeled cells were counted in a Nexcelom Vision Cellometer equipped with Brightfield & 2 Fluorescence Channels Filter Set 101: Excitation/Emission Peak: 475 nm/535 nm and Filter Set 202: Excitation/Emission Peak: 525 nm/595 nm. The stained cell samples (20 µl) were pipetted into a Nexcelom counting chamber and inserted into the image cytometer. Bright-field and fluorescent images were then captured and analyzed at four different locations by the Cellometer image analysis software to directly determine the cell concentration of fluorescently labelled cells. The mean±standard error is reported from three replicates.

Surface Plasmon Resonance (SPR) Assay

To obtain in vitro confirmation of the binding of the isolated compounds to the purified RACK1 protein, the small compound SD-29 and its structural analog SD29-12 were evaluated for their binding potential with the recombinant RACK1A proteins using the Surface Plasmon Resonance (SPR) chip. SPR experiments were carried out with a Biacore T200 equipped with a CM5 sensor chip. Briefly, recombinant RACK1A cysteine-tagged protein was immobilized on flow cell (FC) 2 in HEPES buffered saline (10 mM Hepes, pH 7.4, and 150 mM NaCl, 3 mM $CaCl_2$)) using a thiol-coupling kit according to the manufacturer's protocol, resulting in immobilization levels of 4580 response units (RU). FC1 was only activated and inactivated and used as a reference. SD-29 stock solution was diluted to a final concentration of 100, 75, 50, 25, 10 µM and 1 µM injected in 10 mM Hepes, 150 mM NaCl, 3 mM $CaCl_2$), 1% DMSO, and 0.5% P20. Each injection was repeated three times for 60 s. FC1 signals were deducted from FC2 for background noise elimination. $KD_{50}$ is calculated by the equation: $KD_{50}=kd/ka$; kd—dissociation rate constant, ka—association rate constant.

Compound Screening

Structure-based screening of two million commercially available diverse compounds was used to screen for small molecules against the RACK1 Y248 phosphorylation site. The diverse set of compounds was preselected in terms of the molecular and topological properties of the RACK1 Y248 binding site. Generation of Receptor Grids for Docking: Grids were generated using Schrodinger's Glide module. Grid center points were determined from the centroid of each protein's cognate ligand. To obtain the centroid, the Cartesian coordinates for each atom in the ligand were extracted and the average for each dimension was taken. To determine the size of the grids, a trial-and-error approach to determine the smallest grid size that would allow for the re-docking of all reference ligands was undertaken. The largest reference ligand as the upper size limit was chosen and a grid size of 20 Å on each side was the minimum to allow for it to dock was found. Thus, the grid size for docking simulations was set at 20 Å. The in-silico screened compounds were rank ordered based on Glide XP scoring function and top 22 compounds were tested in-vitro. Initially, the compounds were screened on crystalized plant structure (PDB: 3DM0) [Ullah H, Scappini E L, Moon A F, Williams L V, Armstrong D L, Pedersen L C. Structure of a signal transduction regulator, RACK1, from *Arabidopsis thaliana*. Protein Sci. 2008; 17:1771-80.], and later human RACK1 crystal structure was deduced by another group (PDB: 4AOW). Strikingly, sequence and structure of the Y248 phosphorylation site and K273 sumoylation sites are 100% identical.

2. Results

Post-translational modifications such as tyrosine phosphorylation and protein sumoylation have been implicated in the regulation of RACK1 function in various organisms [Chang B Y, Chiang M, Cartwright C A. The interaction of Src and RACK1 is enhanced by activation of protein kinase C and tyrosine phosphorylation of RACK1. J Biol Chem. 2001; 276:20346-56; Yang X J, Grégoire S. A recurrent phospho-sumoyl switch in transcriptional repression and beyond. Mol Cell. 2006; 23:779-86]. Mutagenesis work has identified Tyr246 as a potential phosphorylation site and has suggested a correlation between enhanced tyrosine phosphorylation of RACK1 and binding of RACK1 to Src tyrosine kinase [Chang B Y, Chiang M, Cartwright C A. The interaction of Src and RACK1 is enhanced by activation of protein kinase C and tyrosine phosphorylation of RACK1. J Biol Chem. 2001; 276:20346-56]. In plants, tyrosine phosphorylation by dual-specificity serine/threonine/tyrosine kinase has been proposed [Rudrabhatla P, Reddy M M, Rajasekharan R. Genome-wide analysis and experimentation of plant serine/threonine/tyrosine-specific protein kinases. Plant Mol Biol. 2006; 60:293-319]. The Y248 residue of *Arabidopsis* RACK1A protein is the conserved residue that corresponds to the human RACK1 Y246 site in a sequence alignment [Ullah H, Scappini E L, Moon A F, Williams L V, Armstrong D L, Pedersen L C. Structure of a signal transduction regulator, RACK1, from *Arabidopsis thaliana*. Protein Sci. 2008; 17:1771-80]. The RACK1A crystal structure showed that the side chain of Tyr248 (Y248) in the RACK1A protein is located at the end of the loop connecting pi-strands A and B of blade 6, and is fully exposed to the solvent making it easily accessible for modification [Ullah H, Scappini E L, Moon A F, Williams L V, Armstrong D L, Pedersen L C. Structure of a signal transduction regulator, RACK1, from *Arabidopsis thaliana*. Protein Sci. 2008; 17:1771-80]. Recently, it was shown that mutagenesis of Y248F abolished the homo-dimerization potential of RACK1A proteins [Kundu N, Dozier U, Deslandes L, Somssich I E, Ullah H. *Arabidopsis* scaffold protein RACK1A interacts with diverse environmental stress and photosynthesis related proteins. Plant Signal Behav. 2013; 8:e24012]. Moreover, while wild-type RACK1A scaffold protein, when used as bait, could interact with almost 100 different proteins, RACK1A-Y248F bait failed to interact with any protein [Kundu N, Dozier U, Deslandes L, Somssich I E, Ullah H. *Arabidopsis* scaffold protein RACK1A interacts with diverse environmental stress and photosynthesis related proteins. Plant Signal Behav. 2013; 8:e24012], implicating the residue in the functional regulation of RACK1 protein. It is quite possible that post-translational modifications, like Y248 phosphorylation, are needed to stabilize the RACK1A protein [Sabila M, Kundu N, Smalls D, Ullah H. Tyrosine Phosphorylation Based Homo-dimerization of *Arabidopsis* RACK1A Proteins Regulates Oxidative Stress Signaling Pathways in Yeast. Front Plant Sci. 2016; 7:176; Link A J, Eng J, Schieltz D M, Carmack E, Mize G J, Morris D R, Garvik B M, Yates J R 3rd. Direct analysis of protein complexes using mass spectrometry. Nat Biotechnol. 1999; 17:676-82; Ji H, Fraser C S, Yu Y, Leary J, Doudna J A. Coordinated assembly of human translation initiation complexes by the hepatitis C virus internal ribosome entry site RNA. Proc Natl Acad Sci USA. 2004; 101:16990-95; Guo J, Wang S, Valerius O, Hall H, Zeng Q, Li J F, Weston D J, Ellis B E, Chen J G. Involvement of *Arabidopsis* RACK1 in protein translation and its regulation by abscisic acid. Plant Physiol. 2011; 155:370-83; Coyle S M, Gilbert W V, Doudna J A. Direct link between RACK1 function and localization at the ribosome in vivo. Mol Cell Biol. 2009; 29:1626-34]. Considering that RACK1 proteins homo/hetero-dimerize, it is hypothesized that the dimerization status of RACK1 proteins, dependent on Y248 residue phosphorylation, may dictate the regulation of specific signaling pathways by fine tuning affinities for interacting proteins [Sabila M, Kundu N, Smalls D, Ullah H. Tyrosine Phosphorylation Based Homo-dimerization of *Arabidopsis* RACK1A Proteins Regulates Oxidative Stress Signaling Pathways in Yeast. Front Plant Sci. 2016; 7:176].

As viruses require host factors to translate their transcripts, targeting the host factor(s) offers a unique opportunity to develop novel antiviral drugs. In addition, the low variability of host factors targeted by host-targeted antivirals (HTAs) results in a high genetic barrier to resistance [Nathan C. Fresh approaches to anti-infective therapies. Sci Transl Med. 2012; 4:140sr2]. In this regard, we report here the identification of inhibitor compounds for the host protein RACK1, a protein that is utilized by many viruses for their own proliferation. The requirement for the Y248 residue phosphorylation for both homo-dimerization and interaction with diverse proteins has led us to target the site for isolating small compounds that could bind the Y248 pocket and thus prevent its phosphorylation. We hypothesized that functional inhibitor compounds of RACK1 may prevent the proliferation of those viruses that use host RACK1 protein for their mRNA translation.

Figure 2A:
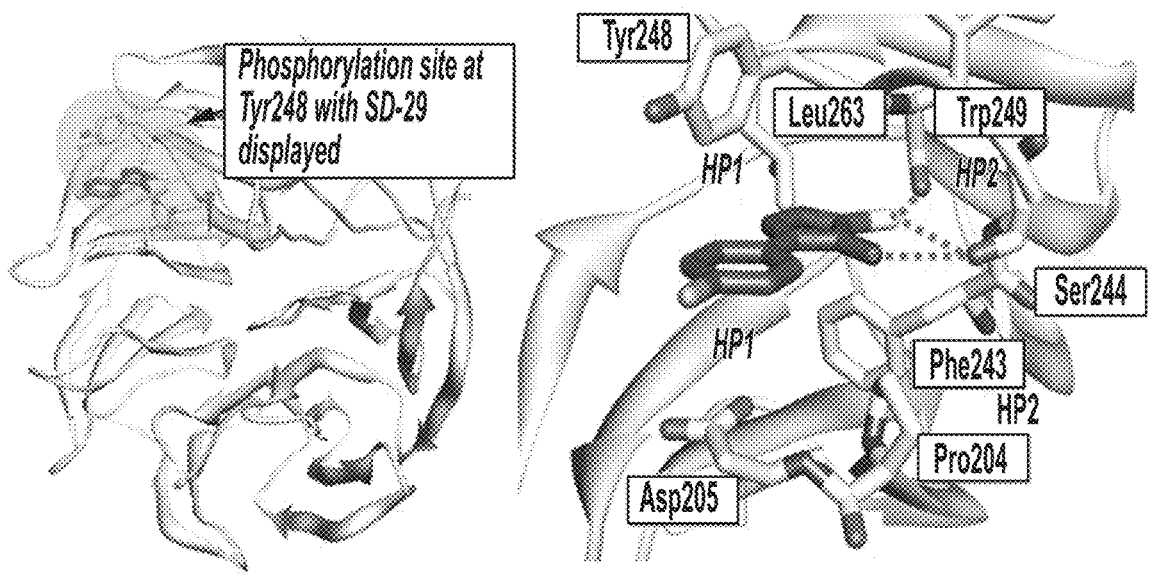
FIG. 2A shows docked Model of RACK1A with SD-29 at the Y248 phosphorylation site. (left panel) Modeled structure of RACK1A with SD-29 (carbon in green) docked into it. The targeted binding pocket is highlighted in green. RACK1A is shown as a ribbon model (white). (right panel) Detailed view of the SD-29 (carbon in green) interaction with RACK1A site pocket. The residues interacting with SD-29 are shown in a ball-and-stick model. Hydrogen bonds are shown as red broken lines. SD-29 binding site is surrounded by both hydrophobic (HP1) and hydrophilic residues (HP2). The structural model of 'SD-29' with RACK1A showing hydrogen bonds with Ser244, Trp249 and hydrophobic interactions with Tyr248, Phe243, Pro204, Leu 263 and Trp249 residues.
Figure 2B:
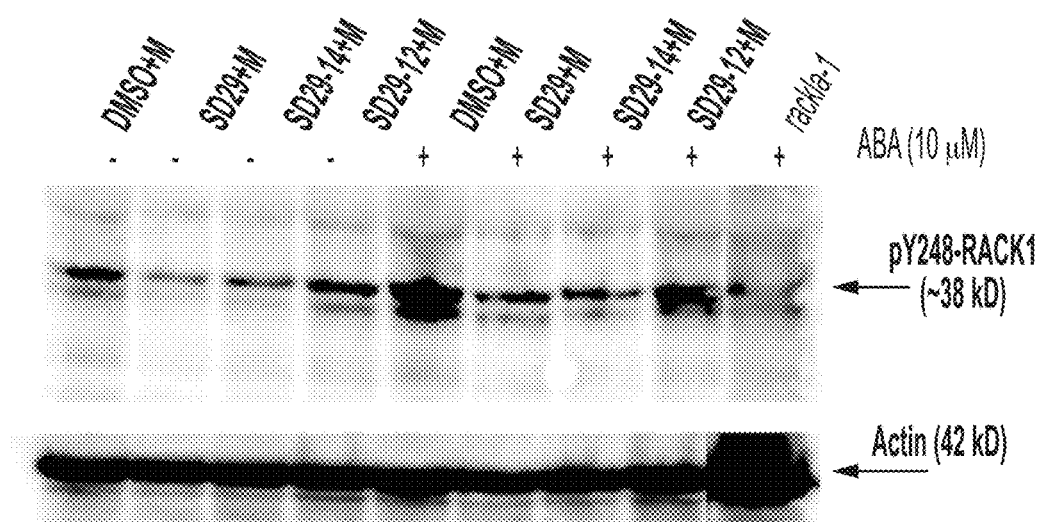
FIG. 2B shows a result demonstrating that RACK1 functional inhibitor compounds inhibit stress hormone induced RACK1A Y248 phosphorylation. One-week old *Arabidopsis* seedlings were treated with 10 μM of stress hormone Abscisic acid (ABA) in the presence/absence of the inhibitor compounds for 12 hours in a growth chamber (overnight) at 22° C. Lysates were probed with an antibody raised to detect phosphorylated Y248 residue of RACK1A protein in *Arabidopsis*. Lysates from rack1a-1 knock-out mutant seedlings grown and treated similarly as the wild-type seedlings were used as a negative control. The compounds were dissolved in DMSO (D) and ABA was dissolved in methanol (M). The lower panel shows the same membrane stripped with stripping buffer and then probed with an *Arabidopsis* Actin antibody to show the loading control.

SD-29 is Identified as a Potent Binder to the RACK1A Y248 Phosphorylation Pocket By the implementation of a structure based drug design approach, the best-fitting candidate RACK1A Y248 pocket binding small compound-SD-29 the 4-amino-5-phenyl-1,2,4-triazole-3-thiol class of compounds has been identified and its analogs are used to provide precise regulation of reported RACK1 mediated specific viral proliferation. To isolate the best-fit compounds, the multi-step screening approach, in which each step acts as a filter comprised of protein conformation sampling to account for flexibility of unbound proteins prior to docking simulations, has been used. To generate the pharmacophore model, the relative positions of the donor/acceptor sites and hydrophobic centers were used as potential pharmacophore sites. The acceptor (A), donor (D), hydrophobic sites, and negative/positive centers were defined with various macro, spatial and constraints features with exclusion spheres centered on the receptor site. A pharmacophore match search was performed on a small molecule database that contains five million commercially available compounds, including natural product compounds. FIG. 1A shows a receptor-based pharmacophore model generated on the Y248 RACK1A site (phosphorylation site) with exclusion spheres. To get appropriate docking, the exclusion spheres were used up to 8A region from the binding site region. Using this strategy, a candidate compound, SD-29 that putatively binds to RACK1A Y248 (FIG. 2A) has been identified. Using the identified SD-29 structure, a ligand pharmacophore model with various macros, spatial and constraints features defining centroid, acceptor (A), donor (D), and hydrophobic sites/centers was developed to aid in further identification of additional compounds (FIG. 1B).

FIG. 2A shows the docked model of RACK1A with the most potent small compound (SD-29) at the Y248 phosphorylation pocket. The detailed view of SD-29 (carbon in green) interaction with the RACK1A binding site, indicates that SD-29 potentially form hydrogen bond with Ser244 and Trp249, and maintains hydrophobic interactions with Try248, Phe204, Leu263, and Trp249 residues. In order to obtain in vitro confirmation of the binding of the isolated compounds to the purified RACK1A protein, recombinant RACK1A protein from rice was raised in *E. coli* cells (FIG. 2D). The small compound SD-29 and its structural analog (SD29-12) were used to evaluate their binding potential with the recombinant RACK1A proteins. The compounds were examined for their ability to interact directly with wild-type recombinant protein immobilized on the Surface Plasmon Resonance (SPR) chip. The SPR assays showed that the compounds SD-29 and SD29-12 bound strongly to recombinant RACK1A protein with an $KD_{50}$ value of 42 μM and 58 μM, respectively (FIG. 2E). This in-vitro confirmation of binding of the compounds to RACK1A protein has led to us to investigate whether the binding has any effect on the reported host factor RACK1 mediated virus proliferation.

Compounds can Potentially Inhibit Stress-Induced RACK1A Y248 Phosphorylation

In order to evaluate whether SD-29 can specifically inhibit RACK1A tyrosine phosphorylation, particularly on the Y248 residue, an anti-phospho-Y248-RACK1 antibody was raised commercially (Creative Diagnostics, NY). To ascertain whether the antibody only recognizes the *Arabidopsis* Y248 in the RACK1A protein, and not in the RACK1B or RACK1C proteins, the RACK1A-specific phospho-peptide (10 residues) was adsorbed against the non-phosphorylated RACK1A, RACK1B and RACK1C peptides and the adsorbed phospho-peptide was used as the antigen in rabbit. RACK1A Y248 phosphorylation has previously been identified as a key event needed for RACK1 mediated scaffolding activities by regulating protein-protein interactions in plants [Kundu N, Dozier U, Deslandes L, Somssich I E, Ullah H. *Arabidopsis* scaffold protein RACK1A interacts with diverse environmental stress and photosynthesis related proteins. Plant Signal Behav. 2013; 8:e24012; Sabila M, Kundu N, Smalls D, Ullah H. Tyrosine Phosphorylation Based Homo-dimerization of *Arabidopsis* RACK1A Proteins Regulates Oxidative Stress Signaling Pathways in Yeast. Front Plant Sci. 2016; 7:176.]. The corresponding residue in human RACK1 is also a key requirement for scaffolding activities needed at the receptor level [Chang B Y, Chiang M, Cartwright C A. The interaction of Src and RACK1 is enhanced by activation of protein kinase C and tyrosine phosphorylation of RACK1. J Biol Chem. 2001; 276:20346-56]. As RACK1A is known to regulate the diverse stress responses in plants [Islas-Flores T, Rahman A, Ullah H, Villanueva M A. The Receptor for Activated C Kinase in Plant Signaling: Tale of a Promiscuous Little Molecule. Front Plant Sci. 2015; 6:1090], we investigated the role stress hormone abscisic acid on the RACK1A Y248 phosphorylation. It is known that ABA mediated signaling pathways regulate diverse biotic and abiotic stresses including salt and drought stresses [Fernando VCD, Schroeder D F. (Feb. 17th 2016). Role of ABA in *Arabidopsis* Salt, Drought, and Desiccation Tolerance, Abiotic and Biotic Stress in Plants—Recent Advances and Future Perspectives, Shanker A K and Shanker C, IntechOpen] and RACK1A has been implicated in the ABA mediated stress pathways in *Arabidopsis* [Guo J, Wang J, Xi L, Huang W D, Liang J, Chen J G. RACK1 is a negative regulator of ABA responses in *Arabidopsis*. J Exp Bot. 2009; 60:3819-33]. Therefore, we used young *Arabidopsis* seedlings treated with/without ABA for 12 hours to mimic stress conditions. As a control, we used lysates from the rack1a-1 knock-out seedlings. While the actin antibody shows the almost equal loading, the presence or absence of ABA showed a significant role on the RACK1A Y248 phosphorylation (FIG. 2B). The lane with ABA but no inhibitor compounds clearly showed that the Y248 residue of RACK1A proteins were highly phosphorylated, while the inhibitor compounds (SD 29 and SD 29-14) prevented the ABA-induced Y248 phosphorylation which showed almost as the same level without the stress hormone present (FIG. 2B). Note that, the antibody was raised by using RACK1A Y248 phosphorylated peptide as immunogen and by adsorbing against the non-phosphorylated RACK1A, RACK1B, and RACK1C peptides. Comparing with the negative control and considering the scheme to raise the antibody, it can be asserted that the SD29, SD29-14, and SD29-12 to a lesser extent, can potentially inhibit the stress induced Y248 phosphorylation.

Figure 2C:
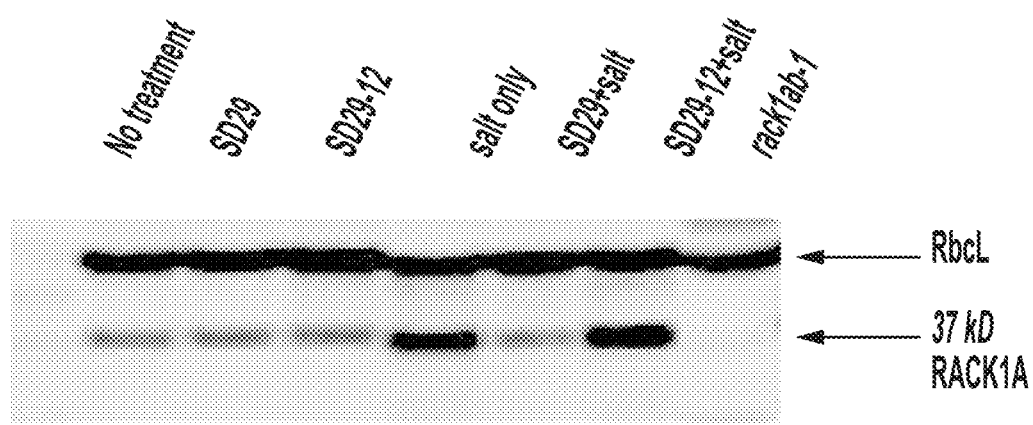
FIG. 2C shows a result demonstrating that salt stress-induced upregulation of RACK1 expression was inhibited by SD-29. The abundant leaf protein Rubisco large subunit (RbcL) was used as a loading control for the blot. The 37 kD RACK1 band was absent from the genetic knockout of RACK1 plants (double mutant-rack1ab lane).
Figure 2D:
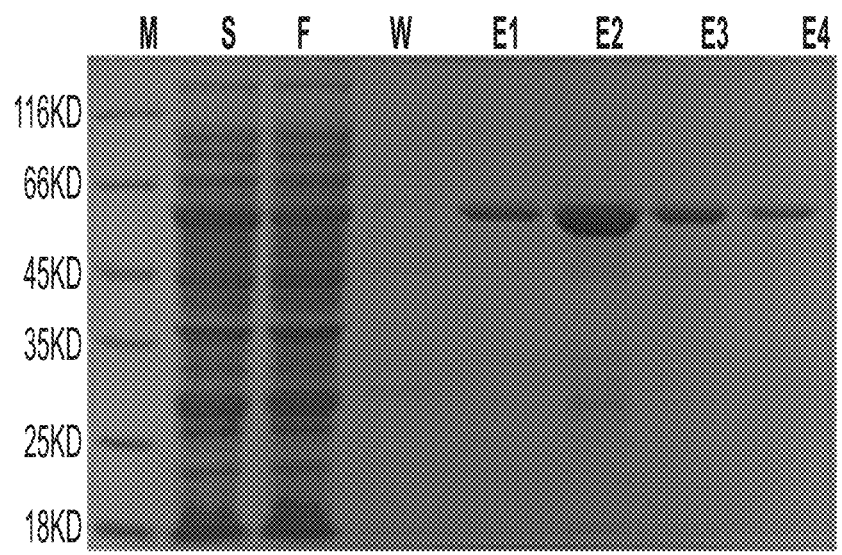
FIG. 2D shows purified RACK1 protein on a SDS-PAGE gel. *E. coli* BL21(DE3) host strain was transformed with recombinant plasmid containing rice RACK1 (Chr05Os05g47890) cDNA with a 3' His tag. PMSF-induced bacterial lysate eluted from the glutathione-resin column was resolved by the SDS-PAGE electrophoresis for purity check. Lane M: Protein Marker; Lane S: Supernatant; Lane F: Flow through of supernatant; Lane W: Wash; and Lane E1~4: Elutions.
Figure 2E:
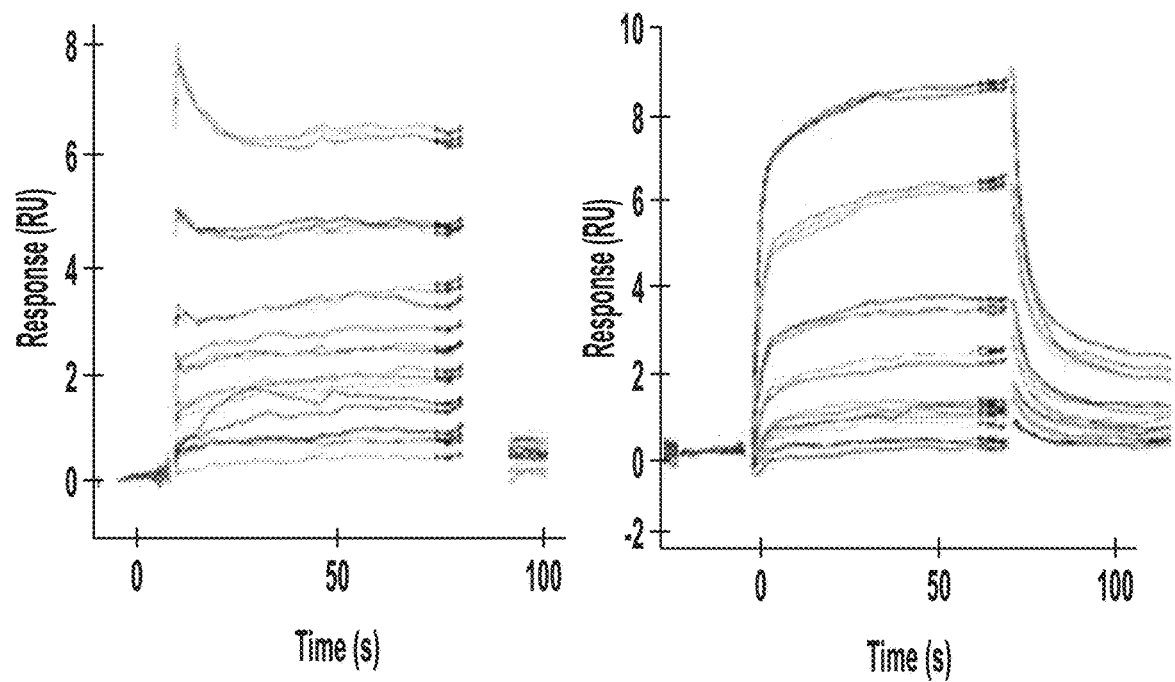
FIG. 2E shows a result demonstrating that in the SPR assay, SD-29 (left panel) and SD-29-12 (right panel) bind directly to immobilized RACK1A on the surface of the chip via similar patterns, as evident in the sensogram. SD-29 (left panel) and SD-29-12 (right panel) were separately injected three times on the CM5 chip at 0, 1.56 μM, at 3.13 μM, 6.25 μM, 12.5 μM, 25 μM, 50 μM, and 100 μM (top sensor) concentrations (left panel) and at 3.13 μM, 6.25 μM, 12.5 μM, 25 μM, 50 μM, and 100 μM (top sensor) concentrations (right panel).

The reported positive expression of RACK1A protein under salt stress condition in *Arabidopsis* has led us to examine the RACK1A expression in the presence and absence of the inhibitor compounds during salt stresses. We determined that the RACK1A protein expression was specifically modulated by the inhibitor compounds when the lysates with salt or without salt in the presence and absence of the small compounds were probed with an antibody raised by using the full length RACK1A protein as antigen (Agrisera, Vännäs, Sweden, FIG. 2C). When challenged with salt stress, SD-29, but not its analog SD29-12, inhibited RACK1 protein expression. However, whether the effect of SD29-12 is *Arabidopsis* salt stress specific condition needs further experimental evidence. As the antibody cross-reacts with all three RACK1 isoforms in *Arabidopsis*, we used the double knockout (rack1ab) as a negative control on the blot (triple mutant is lethal at the early seedling stage). The large subunit of the abundant leaf protein rubisco (RbcL) was used as loading control for this blot. As the results support the in-silico based prediction, we set out to investigate the effect of the compounds on the mammalian RACK1 based virus proliferation.

HSV-1 Infection Induced RACK1 Expression

Since RACK1 is an important factor for protein translation, we wondered whether RACK1 expression is regulated by viral infection. We tested this hypothesis in a HSV-1 infection system in the HEp-2 cell line. This cell line was selected because the human RACK1 target site Y246 shows strong similarity to the *Arabidopsis* Y248 pocket. First, we infected HEp-2 cells with HSV-1 at an MOI of 1.25. The whole cell lysates were collected at different time points as indicated in A of FIG. 3. The samples were run on an SDS PAGE gel and the proteins were transferred to a membrane which was blotted with antibodies for viral proteins (ICP0, ICP8, and gD) and for cellular proteins (RACK1 and tubulin). RACK1 was induced at the very beginning of the viral infection (2 hpi), as can be seen by comparing the levels of RACK1 after viral infection to that of 0 hpi (A of FIG. 3). The increasing protein level of RACK1 reached its peak at 8 hpi. We then wondered whether RACK1 upregulation is related to the viral concentration. For that purpose, we infected HEp-2 cells with different MOIs of HSV-1 for 24 hours to examine the levels of RACK1. RACK1 levels were increased after viral infection and the increase in RACK1 was proportionally associated with the MOI of virus (A of FIG. 3). Therefore, HSV-I infection induces the production of RACK1 at very early time points after infection and the level of RACK1 upregulation is dependent on viral dose. In addition, as expected all the viral proteins were up-regulated with increasing viral loads and at increasing time-points (A of FIG. 3). The results helped establishing the concentration and time-points needed to see whether the compounds have any effect on the viral proliferation that is marked by the increasing synthesis of viral proteins.

SD-29 has Repressive Effects on Viral Protein Production

To determine whether the small compound SD-29 that binds to RACK1A protein and inhibits Y248 phosphorylation, has any effects on viral protein production, we treated HEp-2 cells with SD-29, its analogue (SD29-12), or DMSO for 24 hours at 100 µM, and then the cells were infected with different MOIs of HSV-1 (B of FIG. 3). Twenty-four hours after infection, the whole cell lysate samples were subjected to western blot assay to examine the viral and cellular proteins. SD-29 reduced the production of RACK1 as compared to the DMSO or SD-29-12 control treatment groups (B of FIG. 3). Clearly, viral protein levels from SD-29-treated HEp-2 cells were lower than that of DMSO- or SD-29-12-treated HEp-2 cells. We examined three HSV-1 proteins: ICP0 is an immediate early (IE) protein, ICP8 is an early (E) protein, and gD is a late (L) protein. Therefore, our results demonstrated that SD-29 repressed HSV-1 protein production, which can effectively inhibit virus proliferation in the cell line.

Compound's Effect on HSV-1 Gene Transcription

Figure 4:
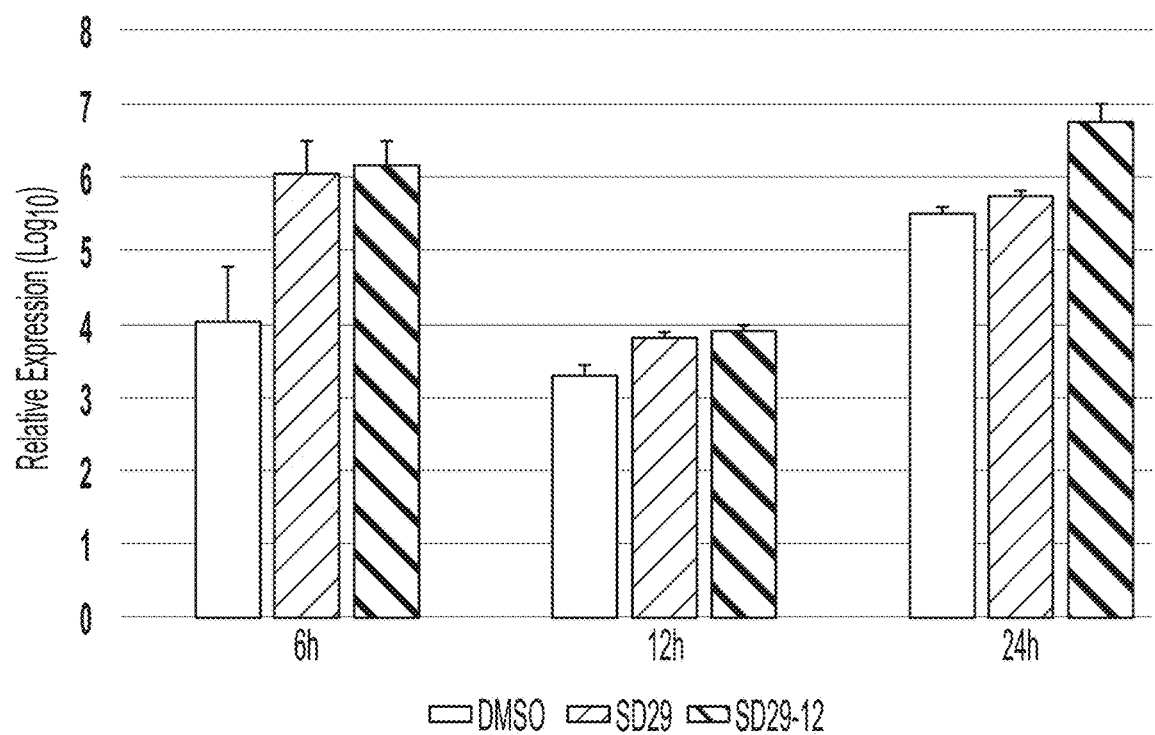
FIG. 4 shows a real-time PCR analysis of HSV-1 ICP0 expression in Hep-2 cells treated with the indicated inhibitor compounds and DMSO (as control) for the indicated time points. The total transcript levels were quantified using actin expression as an internal control. The cDNA obtained immediately after the virus and drug transfection(s) was set as a baseline value. The normalized expression values were transformed to the log 10 value. The data plot represents mean t standard error calculated from three replicates.

Since RACK1 is an important chaperone protein for ribosome function in mRNA translation, we assumed that SD-29 might affect viral gene expression only at the translational level. The compounds were developed to specifically inhibit the RACK1 protein; therefore, it is not expected to affect the mRNA production of assayed proteins (FIG. 3). To investigate whether SD-29 is functioning as expected, the mRNA expression level of the ICP0 gene was measured in qPCR assay (FIG. 4). Though initially after the infection, the HSV-1 ICP0 transcript level was upregulated to some extent by the compounds, over time the effect subsided and fall at the same level as with the DMSO treated samples (FIG. 4). Note that the assayed gene ICP0 is an immediate early gene and the ICP0 protein is capable of transactivating promoters from all three kinetic classes of HSV-1 genes, including immediate-early, early and late. Therefore, high level of transcripts at the early stage of infection may reflect an adaptive response to the challenge by the compounds. The compound treated (SD-29, SD29-12) and non-treated (DMSO) samples essentially showed the same level of ICP0 mRNA at 12 and 24 hpi after showing slight upregulation initially (FIG. 4). The results establish the specificity of the SD-29 in inhibiting the level of key proteins needed by the HSV-1 to proliferate while not affecting mRNA levels.

SD-29 Inhibits Viral Proliferation

To assess the efficacy of SD-29 on the HSV-1 proliferation, a plaque assay was performed. We wanted to quantitatively assess whether SD-29 could inhibit viral replication. Because HSV-1 was able to enter cultured HEp-2 cells, we evaluated whether this entry led to productive virus replication. The cytopathic effect in the form of plaque formation increased significantly over time in virus-infected HEp-2 cells treated with vehicle, as seen in Table 1. As shown in Table 1, inoculum harvested from infected HEp-2 cells treated with DMSO produced a larger number of plaques 24 hours post infection. In contrast, cells infected with identical doses of the same virus and treated with SD-29 failed to produce significant infectious virions. These results, together with those of the entry assay, show that treatment with SD-29 led to the inhibition of a productive infection.

TABLE 1

| Plaque formation unit (pfu) assay | | |
| --- | --- | --- |
| DMSO | SD-29 | SD29-12 |
| 0 hpi  0 ± 0 | 0 ± 0 | 0 ± 0 |
| 6 hpi  3.2 ± 0.08 × $10^2$ PFU/mL | 0 ± 0 | 3.8 ± 0.07 × $10^2$ PFU/mL |
| 12 hpi  2.6 ± 0.03 × $10^3$ PFU/mL | 1 ± 0.08 × $10^2$ PFU/mL | 3.6 ± 0.04 × $10^3$ PFU/mL |
| 24 hpi  1.9 ± 0.02 × $10^6$ PFU/mL | 1.8 ± 0.04 × $10^5$ PFU/mL | 2.6 ± 0.03 × $10^6$ PFU/mL |

In Table 1, confluent monolayers of HEp-2 cells were infected with serially diluted HSV-1 virus and were fixed and Giemsa stained at 0, 6, 12, and 24 hr post infection. The numbers of plaques were visualized. The number of plaques formed post infection decreased in the presence of SD-29 in a time-dependent manner.

In order to assess whether the compounds are producing any toxicity that can led to the cell deaths, we evaluated the cell viability by the trypan blue exclusion method. As long-term inhibition of RACK1 expression has been reported to cell cycle arrest, we limited our experimental treatments to 24 h and evaluated the cell viability of almost full confluent cells after 24 h of compound treatment. It can be seen in Table 2, the compounds at 24 h post-treatment did not cause any major cell viability problem as with or without the compounds, the cells maintained over 90% viability.

TABLE 2

HEp-2 Cell viability after 24-hour treatment with 10 or 100 μM concentration of the inhibitor compounds

| Compounds | Mean | Std error (±) |
| --- | --- | --- |
| DMSO (Control) | 96.0 | 4.18 |
| SD-29 (100 μM) | 92.7 | 2.38 |
| SD-29 (10 μM) | 94.0 | 5.79 |
| SD29-14 (100 μM) | 93.7 | 2.17 |
| SD29-14 (10 μM) | 97.5 | 2.06 |
| SD29-12 (100 μM) | 97.7 | 0.43 |
| SD29-12 (10 μM) | 92.7 | 3.96 |

In table 2, the viability of cells was measured with Trypan blue exclusion assay in a Cellometer (Nexcelom, Lawrence, Mass.). The percentage survival of the compound treated cells was evaluated along with the DMSO treated cells. The values represent the mean±SE of three separate well based replicates.

Visualization of the Compound Induced Inhibition of HSV-1 Proliferation

To visualize the effect of the drugs on the proliferation of HSV-1, a luciferase tagged HSV-1 F strain expressing luciferase (R8411 mutant) under the control of ICP27 promoter was obtained [Horsburgh B C, Hubinette M M, Tufaro F. Genetic manipulation of herpes simplex virus using bacterial artificial chromosomes. Methods Enzymol. 1999; 306:337-52]. The co-treatment of the drugs and the virus at the same resulted in a dose dependent lowering of luciferase signals-indicating an inhibitory effect of the compounds (A of FIG. 5). The same samples after incubation of 48 h were used to assay for HSV-1 ICP0 and RACK1 protein expression (B of FIG. 5). Depletion of RACK1 by the compounds correlated with the depletion of the viral ICP0 protein confirming earlier results shown in B of FIG. 3.

Figure 6:
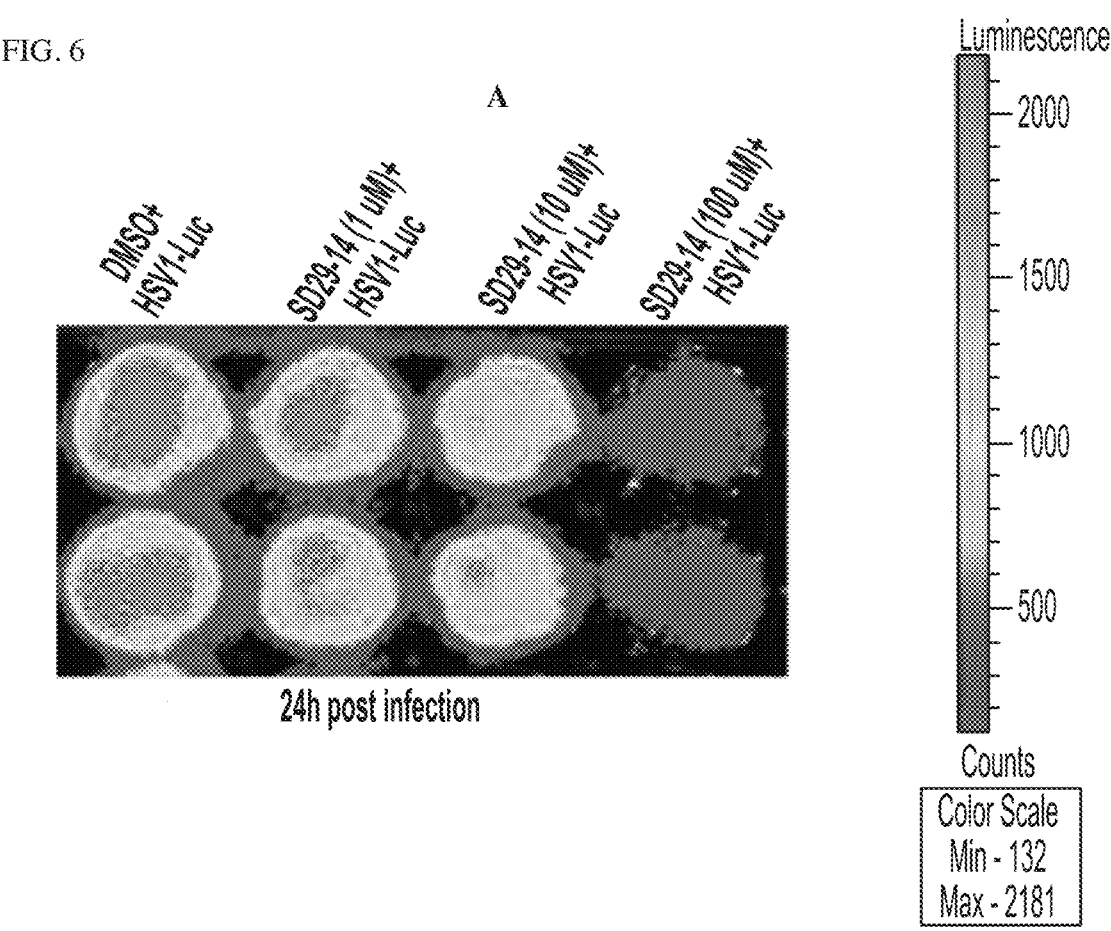
FIG. 6 shows visualization of the RACK1 inhibitor induced inhibition of HSV-1 proliferation in the HEp-2 cells. Panel A of FIG. 6 shows a result demonstrating that the inhibitor compounds effectively inhibited the HSV-1 proliferation, as can be seen in a dose dependent reduction in the luciferase signal (red). Panel B of FIG. 6 depicts the results of quantification of the luciferase signal from the samples in panel (A). Three replicates from two separate experiments were combined to generate the average and the standard error bar.
Figure 6:
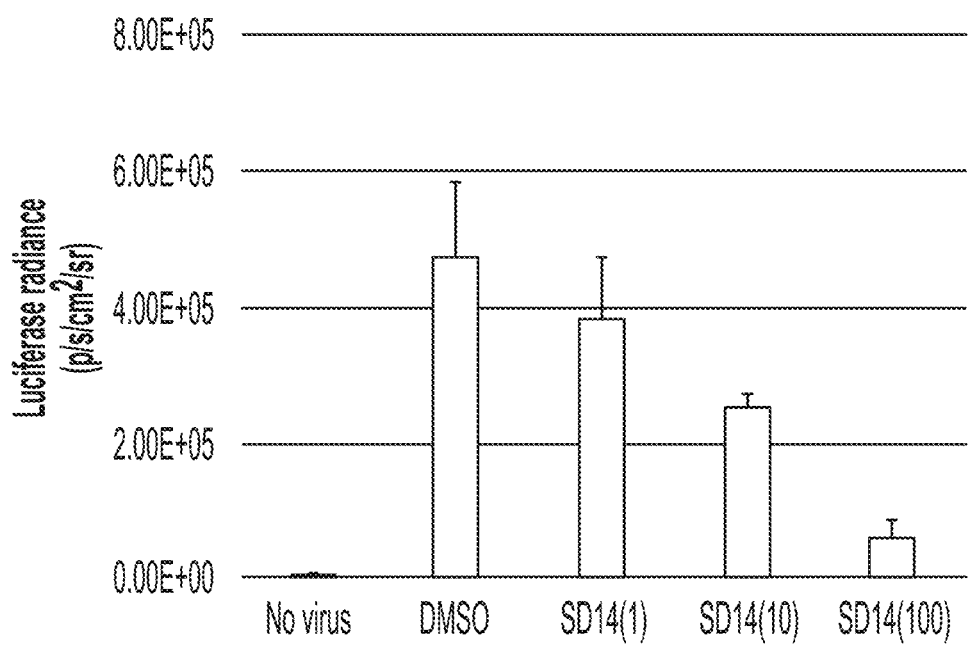

An Analog of SD-29 Reveals Better Efficacy in the Inhibition of HSV-1 Proliferation Through similar docking experiments, an analog with chloro at the meta positions of the phenyl ring (SD29-14) instead of the mono-substituted (fluoro) at the para-position of the phenyl ring (SD-29) was isolated. SD29-14 analog showed strong inhibition of HSV-1 proliferation in a dose dependent manner (A of FIG. 6). While SD-29 showed much less efficacy at the 1 M concentration, SD29-14 significantly inhibited the HSV-1 proliferation as evident by the lower luciferase signals. The luciferase signals were measured quantitively and showed dose dependent inhibitory effect of the SD29-14 on the HSV-1 proliferation (B of FIG. 6). Availability of the compounds with better efficacy will allow application of the compounds at lower concentration which will circumvent any toxicity that higher concentration of compounds may pose. In addition, the better efficacy will allow the compounds to be tested against other IRES utilizing human pathogenic viruses as well.

SD29-14 Inhibits ICP0 Expression

Figure 7:
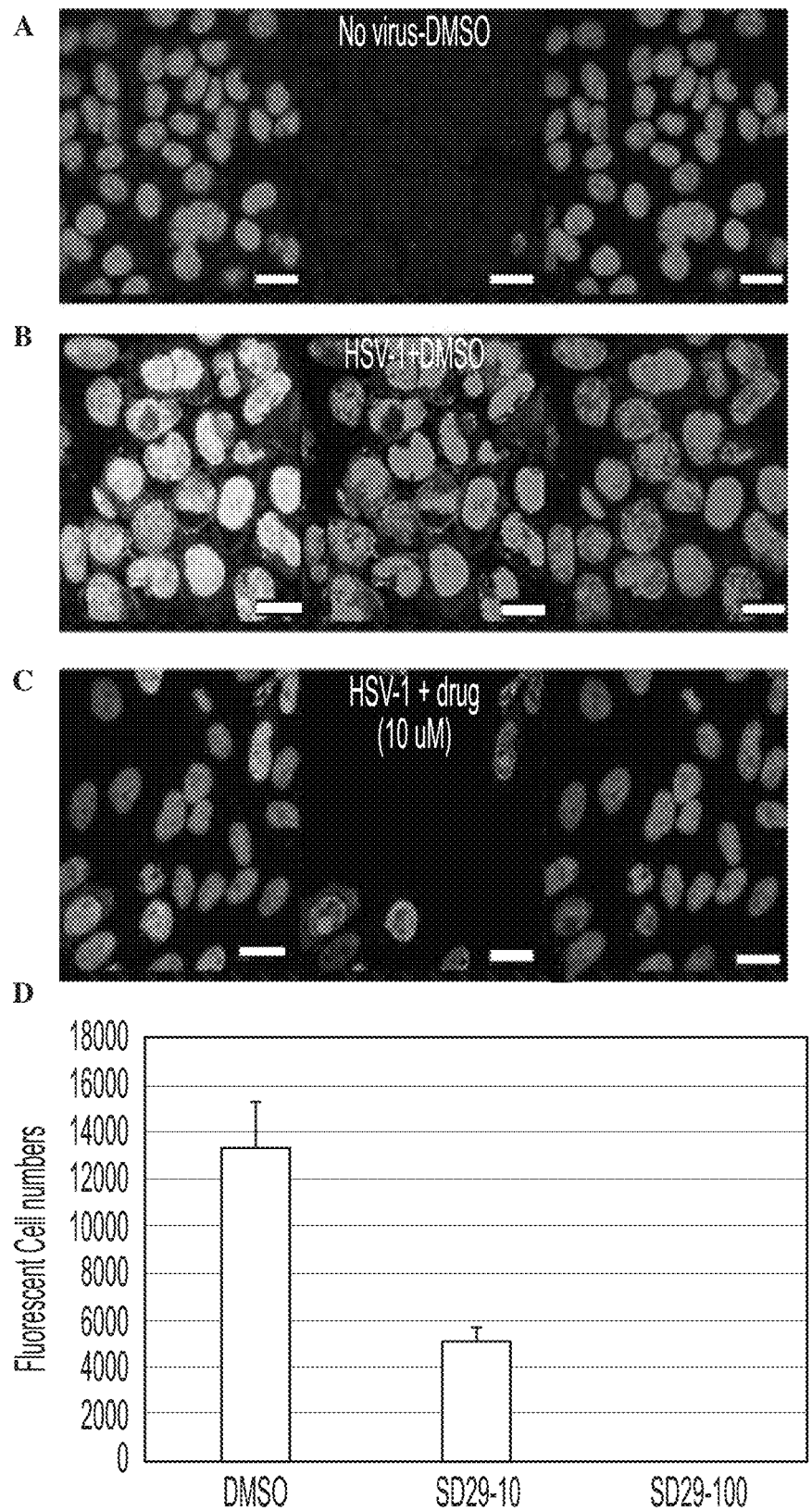
FIG. 7 shows immunofluorescent results for HSV-1 proliferation inhibition by the RACK1 inhibitor compound SD29-14. The HEp-2 cells were infected with HSV-1 at an MOI of 1.0 for 30 h along with the indicated compounds and control. The no-virus control (A), vehicle DMSO treated (B) and SD29-14 10 μM treated (C) cells were fixed with 4% paraformaldehyde and stained with anti-ICP0-FITC (green) and DAPI for DNA (blue) in the nucleus. The slides were observed under a Nikon confocal microscope (60× magnification lens) and pictures were taken to show infected cells (green) and total cells (DAPI). All scale bars correspond to 20 μm. The imaging experiments were performed three independent times, and the results shown represent one of the three experiments. (D) Quantification of fluorescent cells by Image based cell sorting in a Cellometer (Nexcelom Vision). The Y-axis shows the total fluorescent cells per ml. The cells were prepared by immunostaining with ICP0 antibody after 24-h incubation with the indicated compounds. The total cell counts were 1.01×106/ml, 4.69×106/ml, and 5.36×106/ml for DMSO, SD29-14 (10 μM), and SD29-14 (100 μM) respectively. The numbers show the mean±SE of three replicates.

Our results provide evidence for the efficacy of the SD 29-14 against the HSV-1 proliferation, however, to further confirm this we set out to demonstrate via direct visualization the effect of the drugs on the proliferation of HSV-1 in living cells. In this regard, immunofluorescence studies were undertaken where HSV-1 ICP0 protein expression levels were visualized with or without the compounds with higher efficacy (SD29-14) in the Hep-2 cell line. We found that without treatment of the compound, the HSV-1 transfected cells express the viral ICP0 protein uniformly in the nucleus as it overlaps with the nuclear stain DAPI (C of FIG. 7), while treatment with 10 μM concentration of the compound effectively eliminated any expression of ICP0 protein from the cell (C of FIG. 7). The immuno-stained cells without any virus infection were used as a negative control (A of FIG. 7). Note that the absence of FITC stain is not due to the toxicity induced cell death. The DAPI staining of the same cells indicates that viable cells were present, but due to the presence of the compound a significant inhibition of viral proliferation was observed. The results as visualized by the FITC tagged secondary antibody indicate that HSV-1 proliferation is inhibited by the higher efficacy compound SD29-14 with a lower effective concentration.

Comparison of SD29-14 Efficacy with Known Anti-Herpes Drug Acyclovir

Figure 8:
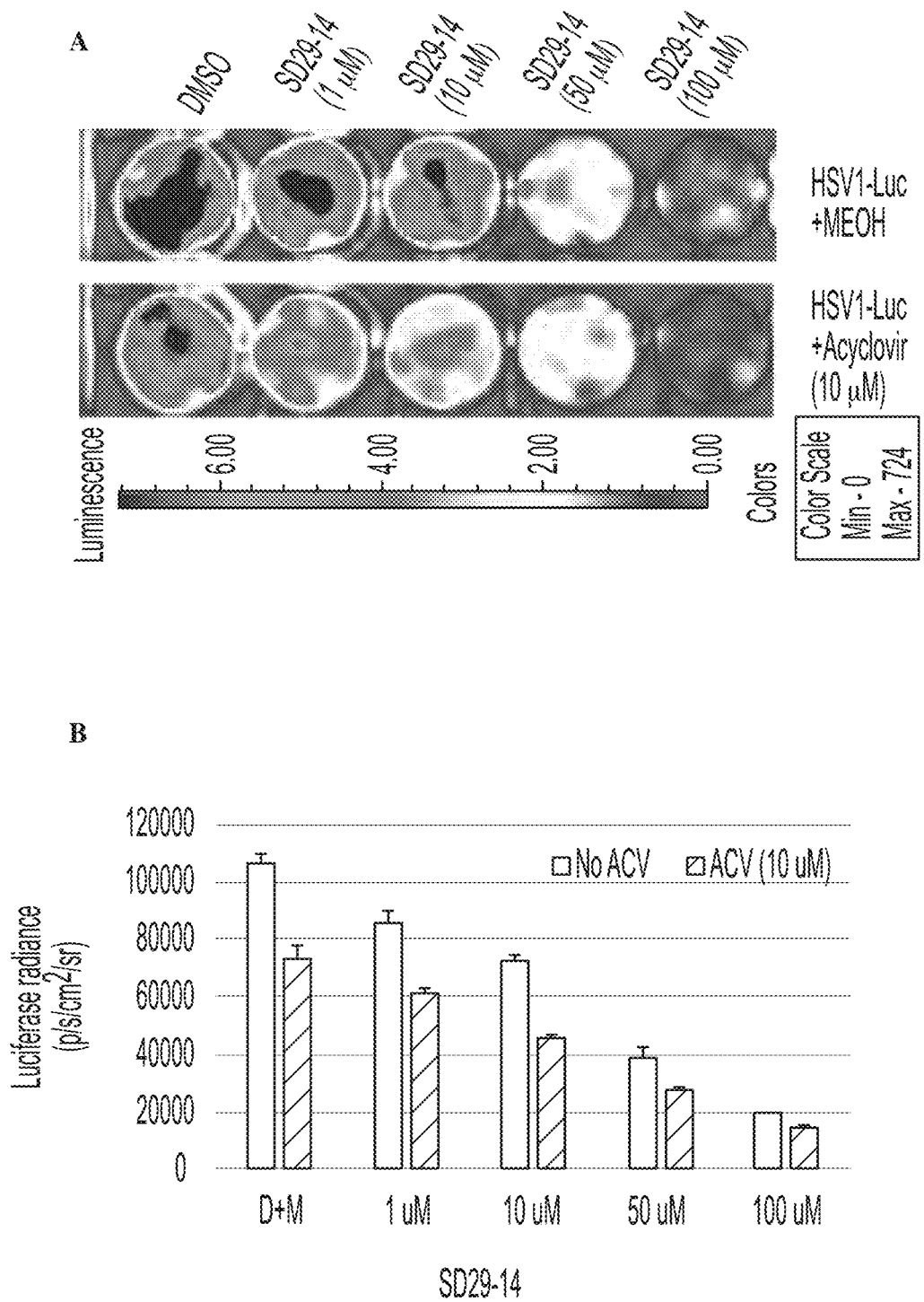
FIG. 8 shows efficacy of SD29-14 compared with anti-herpes drug acyclovir. (A) Hep-2 cells were incubated with the indicated compounds in the presence of HSV1-Luc virus at a concentration of $4 \times 10^6$ pfu/ml media. (B) Quantification of the luciferase signal from the samples in panel (A). Signals from three replicates from two separate experiments were combined to generate the average and the standard error bar.

Acyclovir is the major anti-herpes drug on the market and evaluated the SD29-14 efficacy with that of acyclovir. As can be seen from FIG. 8, application of SD29-14 could effectively inhibit the HSV1-Luc proliferation starting from 1 μM concentration (A of FIG. 8). As very low concentration of acyclovir could not show the significant inhibition of HSV1-Luc (data not shown), we used the concentration of 10 μM at which point the drug showed inhibition of the HSV1-Luc proliferation. Our developed drug appears to show efficacy at slightly higher level than that of acyclovir induced effect. Acyclovir is known to be an inhibitor of viral DNA replication while SD29-14 is not known to regulate the viral DNA replication; therefore, we expected that there will be no interaction between the inhibitory pathways of these two drugs. In the absence of interaction, it is expected that the combinatorial treatment may potentially show synergistic effect in inhibition. Therefore, we treated the virus infected cells with different combination of the drugs. As can be seen from the A of FIG. 8, a supralinear effect is apparent at all different concentrations of SD29-14 combined with 10 μM of acyclovir. When the luciferase signal is quantified, it shows a dose-dependent inhibition of HSV1-Luc proliferation in all concentrations of the drugs used either in combination or SD29-14 alone (B of FIG. 8). We believe this combinatorial application will allow a better approach to combat the HSV1 which is increasingly becoming resistant to the drugs available on the market.

Example 2: Inhibition of HIV-1 and HCV Proliferation

1. Materials and Methods
Cell Culture

Wild-type (wt) Human epithelial type 2 (HEp-2) cells were used, which are known to originate from a human laryngeal carcinoma. HEp-2 cells were generously donated from Dr. Tang's Lab. HEp-2 cells (Passage range between 23-36) were seeded in a growth medium composed of Minimum Essential Medium Eagle (MEME) media with Earle's salts, L-glutamine and sodium bicarbonate (catalog #M4655, Sigma-Aldrich Co. LLC). It was supplemented with 10% (v/v) Fetal Bovine Serum (FBS), (Atlanta Biologicals, Cat #S 1150), 1% Amphotericin B 250 μg/ML, (Fisher Bio-Reagents, Cat #BP2645-50), and 1% (Pen/Strep), 100 U/ml penicillin and 100 g/ml streptomycin, (ATCC® 30-2300™). During general culture, the growth medium was changed every 3 to 5 days. At approximately 70-80% confluence, cells were washed with PBS and passaged (1:9) using 0.25 trypsin-EDTA (Sigma-Aldrich Co. LLC, Cat #T4049). Cells were mixed with Trypan blue solution 0.4% (SIGMA, USA) in 1:1 v/v and counted using a hemocytometer. Cell numbers were recorded, and cells were seeded at the appropriate densities.

HIV-1 VSVG-Pseudotyped Infection

HEp2 cells were infected with VSVG-pseudotyped pNL4-3.Luc.R-E-virus, HIV-1 NL4-3 ΔEnv Vpr Luciferase Reporter Vector (pNL4-3.Luc.R-E-), in which a Firefly luciferase sequence was inserted into the pNL4-3 nef gene, and two frameshifts (5' Env and Vpr aa 26) render this clone Env- and Vpr-. pHEF-VSVG, Vesicular Stomatitis Virus Glycoprotein plasmid, was used as supporting plasmid. Cells were treated with RACK1 inhibitors and its analogs (SD-29, SD-29-12, and SD-29-1) at different concentrations; 1 μM and 100 μM. Moreover, the cells were treated with Dimethyl sulfoxide (DMSO) as a vehicle control or left untreated. DMSO was purchased from Thermo Fisher Scientific (Cat #TS-20688). After (48 hours) incubation, the luciferase activity was measured with Steadylite plus Reporter Gene Assay System, which has the longest-lasting signal for quantitation of firefly luciferase in mammalian cells. Signals were measured using Promega: Modules for the Glo-Max®-Multi Microplate Multimode Reader.

A Dual-Luciferase Reporter Assay

Dual-luciferase reporter constructs were generously provided from (Plank et al., 2013) and (Carvajal et al., 2016). In the plasmid constructs, *renilla* luciferase (Rluc) translation is cap-dependent, while the firefly luciferase (Flue) translation depends on HIV-1 IRES. The Fluc/Rluc ratio was measured in the presence or the absence of the compounds in HEK293T cells transfected with the dual-luciferase plasmid bearing either Beta-globin, HCV, HIV-1 gag, EMVC or HIV-1 ladder sequences. Cells get transfected with the plasmids using Lipofectamine 3000 Reagent, from Thermo Fisher Scientific. Then treated with RACK1 inhibitors and its analogs (SD-29, and SD-29-14) at different concentrations; 1 μM, 10 μM, and 100 μM. Moreover, the cells were treated with Dimethyl sulfoxide (DMSO) as a vehicle control or left untreated. Luc-Pair™ Duo-Luciferase Assay Kit 2.0 Kit (Genecopoeia) was used to measure the luciferase activity. HEK293T cells were grown to reach no more than 90% confluent at the desired time of lysate preparation.

Spectral Un-Mixing of *Renilla* and Firefly Luciferase

For measuring Fluc/Rluc ratio and bioluminescence, Both *Renilla* and Firefly substrates were added to the same wells containing respective plasmid constructs. After the described incubation period, luciferase activity was evaluated from bioluminescence images acquired by a Perkin Elmer IVIS Spectrum Imaging system immediately after adding luciferase substrates. The Spectral Un-mixing options integrated in the software was used to un-mix the respective luminescence from *Renilla* and Firefly. Bioluminescence intensity in each well was quantified in units of photons per second per centimeter squared per steradian ($p/s/cm^2/sr$) by drawing a polygonal region of interest over the signals in images using Living Image 3.0 software (Caliper Life Sciences).

Enzyme-Linked Immune-Sorbent Assay (ELISA)

HIV Type 1 p24 Antigen ELISA was used (RETRO-TEK Cat #0801200). It has been designed for the quantitative measurement of viral antigen from the HIV-1 found in cell culture and other biological fluids such as serum, and plasma. The optical density of each well was read at 450 nm using a microplate reader.

Luciferase assays. CEM T cells were infected with VSVG-pseudotyped virus. Left untreated, or after pretreating the cells with SD-29, SD-29-12 and DMSO (100 uM), the CEM-T cells were infected with pNL4-3.Luc.R-E-virus. Infected cells were then cultured in 6-well plates at 37° C. and 5% $CO_2$. After 48 hrs, 100 uL of cell suspension and 100 uL of reconstituted luciferase buffer (Luclite Kit, Perkin Elmer) was added to each well, and after 10 min incubation, the lysates were transferred into white plates (Perkin Elmer). Luminescence was measured using Labsystems Luminoscan RT equipment (Perkin Elmer).

Remaining cells were collected, washed with PBS and used for western blot.

Infection of CEM-T cells, PBMC, PBL. PBMCs or PBL were activated with phytohemaggultinin (PHA) (0.5 μg/ml) for 48 hrs, followed by interleukin (IL)-2 (10 U/ml) for 24 hrs prior to the infection. CEM-T cells or activated PBMCs or PBL were exposed to T cell tropic viral strains HIV-1 (IIIB) at a multiplicity of infection (MOI) of 0.01 infectious virus/target cell. Cells were treated with SD-29 at indicated concentration at the time of infection. Cells were collected after 6 hrs for viral DNA and 4 days for viral RNA analysis.

Determination of HIV-1 RNA. For quantitative analysis of HIV-1 gag, qPCR was carried out as described earlier (Kumari, N., et al., *Increased iron export by ferroportin induces restriction of HIV-1 infection in sickle cell disease*. Blood Adv, 2016. 1(3): p. 170-183). Primer sequences for HIV gag, forward-ATAATCCACCTATCCCAGTAG-GAGAAAT (SEQ ID NO: 5), reverse-TTGGTCCTGTC-TATGTCCAGAATGC (SEQ ID NO: 6). Mean Cp values for target genes and 18SrRNA were determined and ΔΔCt method was used to calculate relative expression levels.

Plasmids and viruses. HIV-1 proviral vector pNL4-3. Luc.R⁻E⁻ (courtesy of Prof. Nathaniel Landau, NYU School of Medicine, New York, N.Y.) was obtained from the NIH AIDS Research and Reference Reagent Program. HIV-1 (IIIB) strain was obtained from Advanced Biotechnologies.

Antibodies. Antibodies for actin (sc47778) were purchased from Santa Cruz and p55+p24+p17 (ab63917) from Abcam.

Statistical Analysis and Calculations

All assays listed above in this study were run in triplicate unless as indicated. Triplicate is to ensure reproducibility of the data as well as the reliability of the results. All data are presented as a mean±Standard Error of the Mean (SEM) from all experiments.

2. Results

RACK1 Regulates IRES-Mediated Translation in HEK293T Cells Transfected with IRES Plasmids Dual-luciferase reporter constructs were used to determine if the drugs targeting RACK1 affect IRES-mediated translation. *Renilla* luciferase (Rluc) translation dependent on cap and the firefly luciferase (Fluc) translation dependent on HIV-1 IRES were utilized. The Fluc/Rluc ratio was measured in the presence or the absence of the compounds in the HEK293T cells transfected with the dual-luciferase plasmid bearing the predicted IRES from HIV-1 driving a firefly luciferase reporter gene and a cap dependent *renilla* luciferase from the same construct. As a control, HCV IRES is used within the dual luciferase construct (instead of HIV-1) as a positive control as HCV is known to use IRES solely for translating its transcripts, while Beta-globin plasmid was used as a negative control. The dual-luciferase reporters, as used here, are previously reported where HIV-1 IRES were reported (Plank, T. D., J. T. Whitehurst, and J. S. Kieft, Cell type specificity and structural determinants of IRES activity from the 5' leaders of different HIV-1 transcripts. Nucleic Acids Res, 2013. 41(13): p. 6698-714; Carvajal, F., et al., Structural domains within the HIV-1 mRNA and the ribosomal protein S25 influence cap-independent translation initiation. FEBS J, 2016. 283(13): p. 2508-27.) The cells were transfected with the plasmids using Lipofectamine, then treated with RACK1 inhibitors (SD-29 and SD29-14) at different concentrations (1, 10, and 50 µM). Control cells were treated with DMSO or left untreated. SV40 promoter produces a capped and poly-adenylated dicistronic message. Translation of the upstream cistron (*renilla* luciferase, RLUC) is cap dependent, whereas translation of the downstream cistron (firefly luciferase, FLUC) occurs cap independently. The dual luciferase constructs are depicted in FIG. 1A. IRES activity is measured by calculating the ratio of FLUC to RLUC light production (RLUs) (Plank et al., 2013).

Figure 9:
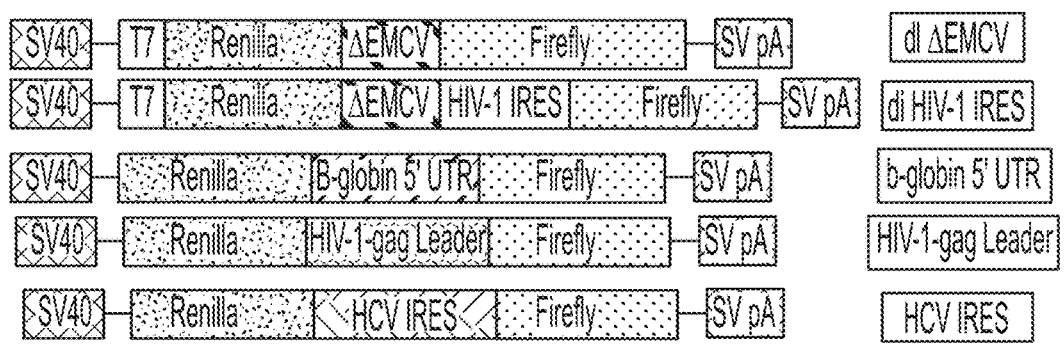
FIG. 9 has Panels A, B and C. Panel A of FIG. 9 shows dual luciferase constructs. Panel B of FIG. 9 shows the relative FLUC (green) and RLUC (Red) signals obtained from the cells by spectral unmixing of the two signals. Panel C of FIG. 9 shows a result demonstrating that while DMSO treated cells produced both FLUC and RLUC signals, the drug treated cells show significant inhibition in the FLUC expression and thereby resulted in the significant inhibition in the overall IRES activity.
Figure 9:
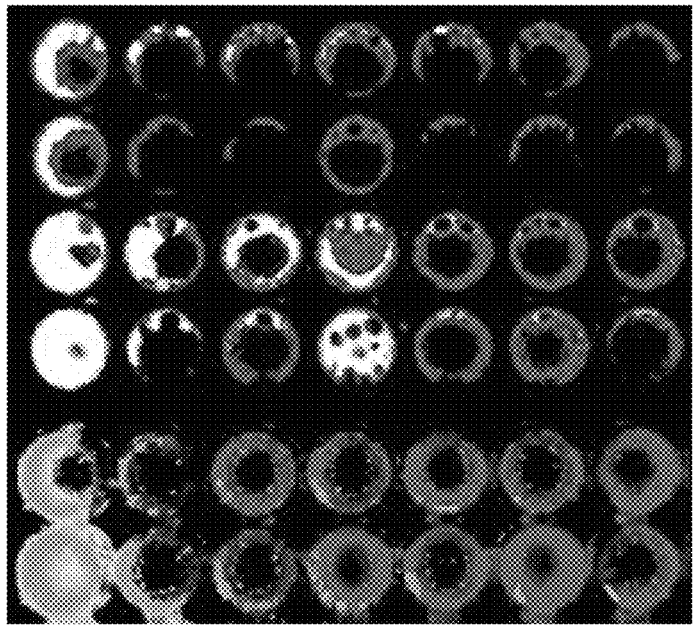
Figure 9:
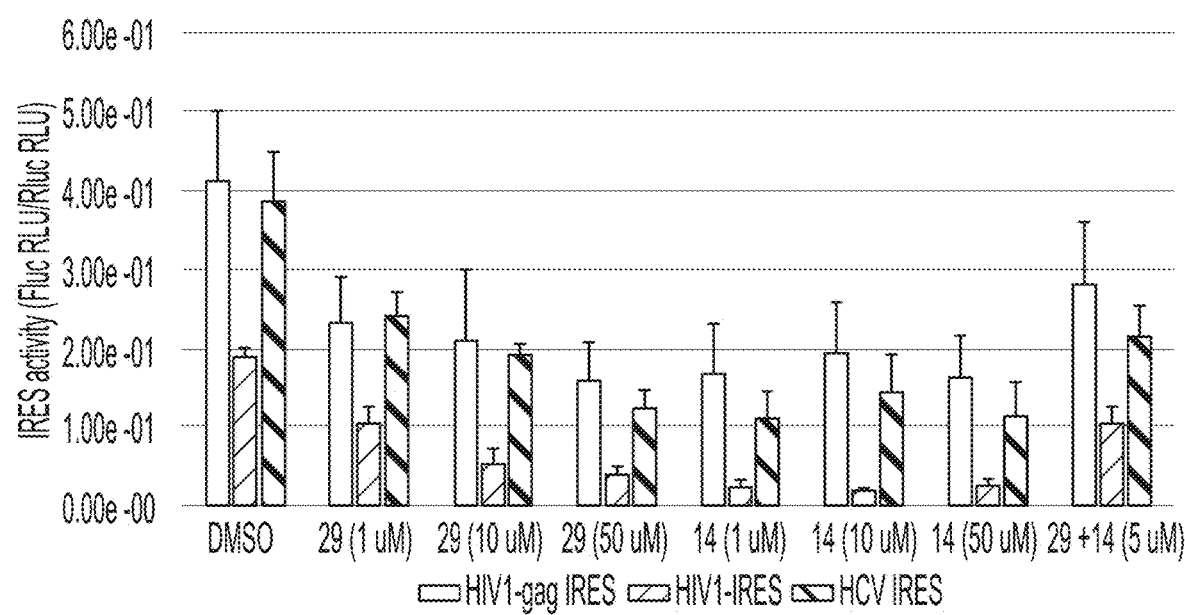
Figure 10:
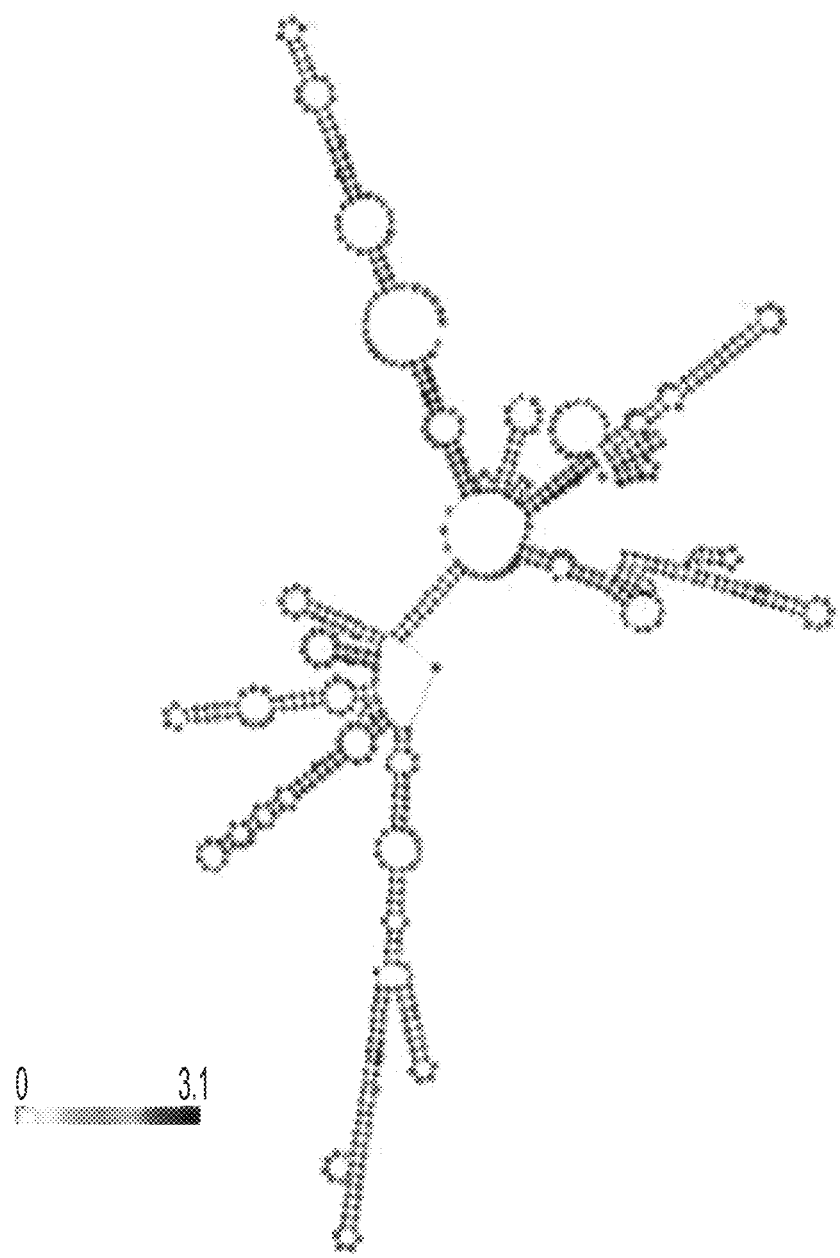
FIG. 10 shows Enterovirus D68 IRES structure, specifically the site for RACK1 interaction. The predicted IRES site of the EV-D68 as computed by the IRESPred web server (Kolekar et al. 2016). Note that the IRESPred reported 189 viruses including HIV-1, Herpes Simplex Virus, and Hepatitis viruses to have IRES in their 5'UTR (Untranslated Region). The structure is deduced from the 1-674 bp of the 5' UTR from the EV-D68 genome (accession number KX433166). The structure is classified to have class 1 with a total of 208 loops of which 13 show potential hairpin loop, one external loop ad 188 internal loops. The sequence contains 11 AUG codons. As the functional RACK1 proteins interacts with the IRES, the RACK1 inhibitor compound of a formula herein prevents the interaction that effectively inhibits viral mRNA translation stopping viral proliferation. The sequence shown in SEQ ID NO: 7 has been used to predict the IRES Structure of the EV-D68 virus.
Figure 11:
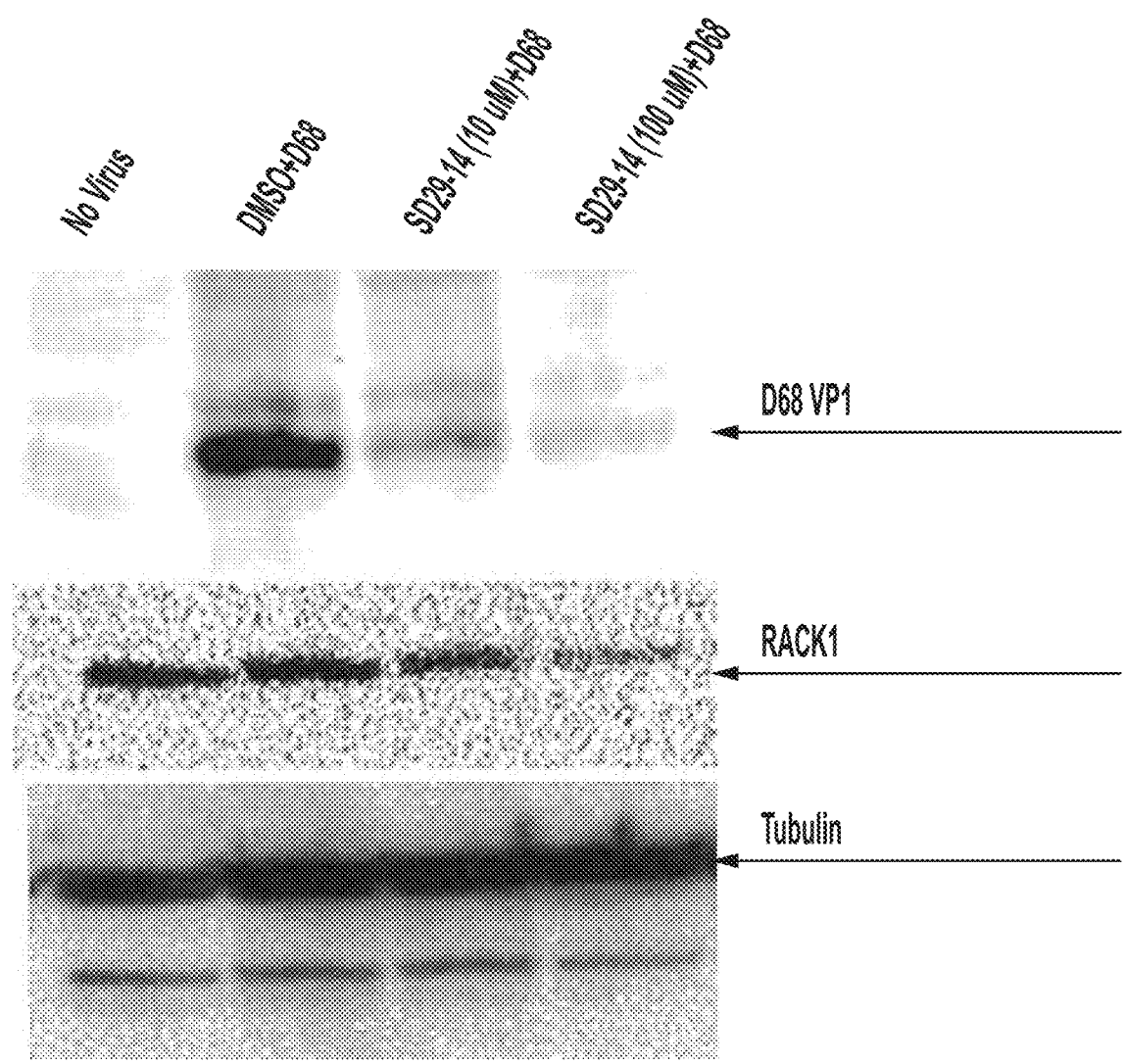
FIG. 11 shows a western assay indicating that SD29-14 inhibits EV-D68 proliferation in a dose dependent way in the HEp-2 cell line. HEp-2 cells were grown to 80-90% confluency in Dulbecco's Modified Eagle's medium (DMEM) supplemented with 10% fetal calf serum (FCS) and 1% penicillin-streptomycin (PS) and fungicide. The virus and the indicated concentration of compounds were added and incubated for 48 h. After washing with PBS, the cell lysates were collected and were run in a Biorad XT-Criterion gel and transferred to a PVDF membrane. The membrane was blotted with an antibody directed against the EVD68 major structural protein VP1 purchased from Genetex (Irvine, Calif.). An anti-mouse IgG-HRP secondary antibody and Biorad's Western ECL substrate-Clarity was used to label the bands and the image was obtained in a Biorad Gel doc system. The top panel shows that compared to the DMSO treated cells with the virus, the SD29-14 treated cells effectively inhibited the viral major structural protein VP1 (arrow). The middle panel shows that the inhibition correlates with the loss of RACK1 protein in the same samples. The tubulin antibody was used as the loading control. Note that the cells without any virus does not show any virus specific band but does show the RACK1 and tubulin expression.
Figure 12:
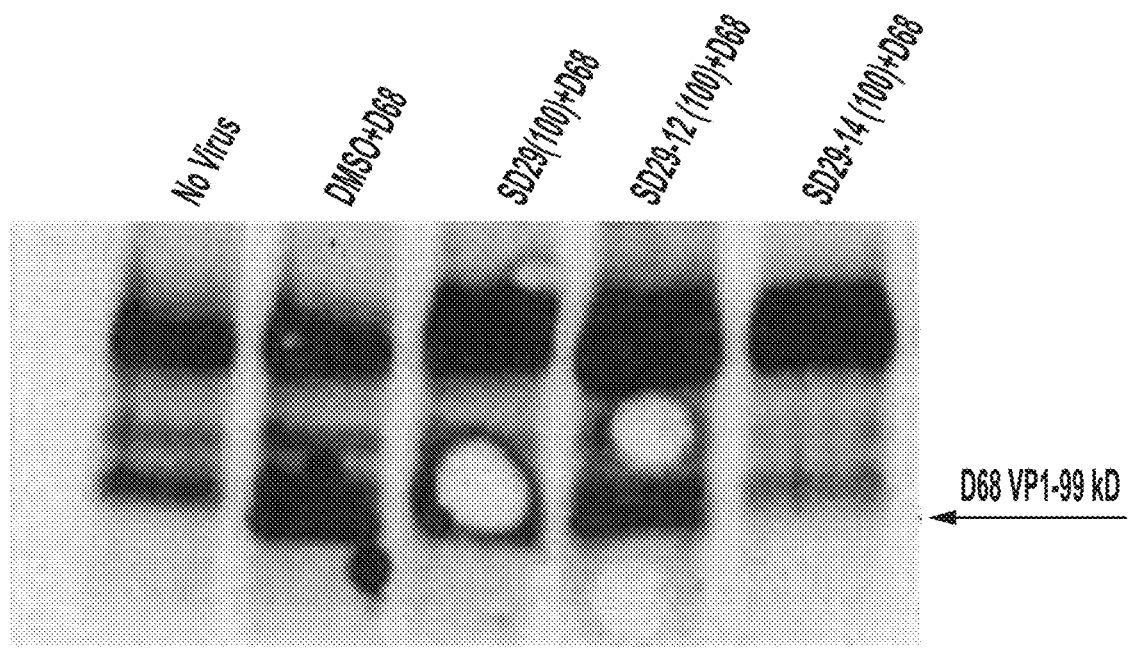
FIG. 12 shows a result demonstrating that SD79-14 shows better efficacy in inhibiting EV-D68 compared with the effect from SD29 and SD29-12. In particular, western assay indicates that SD29-14 inhibits EV-D68 proliferation in an efficient way compared to that of SD29 and SD29-12. HEp-2 cells were grown to 80-90% confluency in Dulbecco's Modified Eagle's medium (DMEM) supplemented with 10% fetal calf serum (PCS) and 1% penicillin-streptomycin (PS) and 1% fungicide. The EV-D68 virus and the indicated concentration of compounds were added and incubated for 48 h. After washing with PBS, the cell lysates were collected and were run in a Biorad Stain free TGX gel and were transferred to a PVDF membrane. The membrane was blotted with an antibody directed against the EV-D68 major structural protein VP1 purchased from Genetex (Irvine, Calif.). An antimouse IgG-HRP secondary antibody and Biorad's Western ECL substrate-Clarity was used to label the bands and the image was obtained in a Biorad Gel doc system. The panel shows that compared to the DMSO, SD29, or SD29-12 treated cells with, the SD29-14 treated cells effectively inhibited the viral major structural protein VP1 (arrow) showing a higher efficacy for the SD29-14 drug. The non-specific band high above the VP1 band indicate that all virus treated lanes were loaded with equal amount of lysates. The identity of the EV-D68 VP1 protein is confirmed by the lack of the 33 kD band in the no virus lane. Note that the SD29-14 treated cells were incubated with EV-D68 for 48 hours; yet the antibody resulted in a band pattern similar to the non-specific band pattern in the no-virus samples—effectively showing the high efficacy of the drug.
Figure 13:
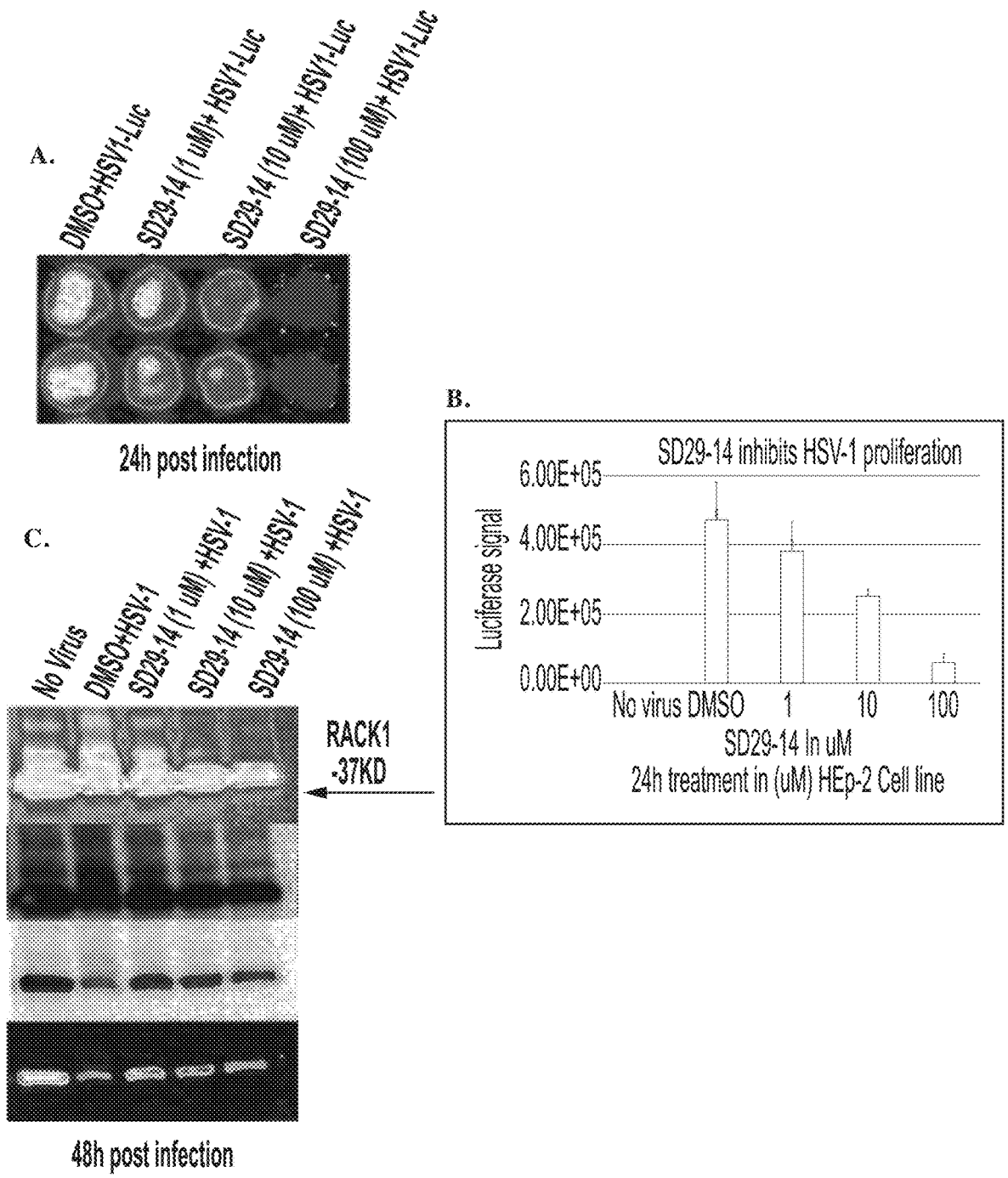
FIG. 13 shows visualization of the RACK1 inhibitor induced inhibition of HSV-1 proliferation in the HEp-2 cells. The virus used in this diagram is an HSV-1 F strain expressing luciferase (R8411 mutant) under the control of the ICP27 promoter and was a gift from Prof. Bernard Roizman (University of Chicago). HEp-2 cells were grown to 80-90% confluency in Dulbecco's Modified Eagle's medium (DMEM) supplemented with 10% fetal calf serum (PCS) and 1% penicillin-streptomycin (PS) and fungicide. The HSV-1 virus and the indicated concentration of compound(s) were added and incubated for 24 h (A of FIG. 13 and B of FIG. 13) and for 48 h in panel C samples. The luciferase signals were imaged and quantified in a Perkin Elmer IVIS Spectrum Imaging system. A of FIG. 13 shows that the inhibitor compound(s) effectively inhibited the HSV-1 proliferation as can be seen in a dose dependent reduction in the luciferase signal (red). B of FIG. 13 shows quantification of the luciferase signal from the samples in panel 1. Three replicates from two separate experiments were combined to generate the average and the standard error bar. C of FIG. 13 shows that the inhibitor compounds reduces the RACK1 phosphorylated bands (higher than the 37 kD RACK1 size). The compound(s) inhibit Y248 phosphorylation of RACK1 protein.
Figure 14:
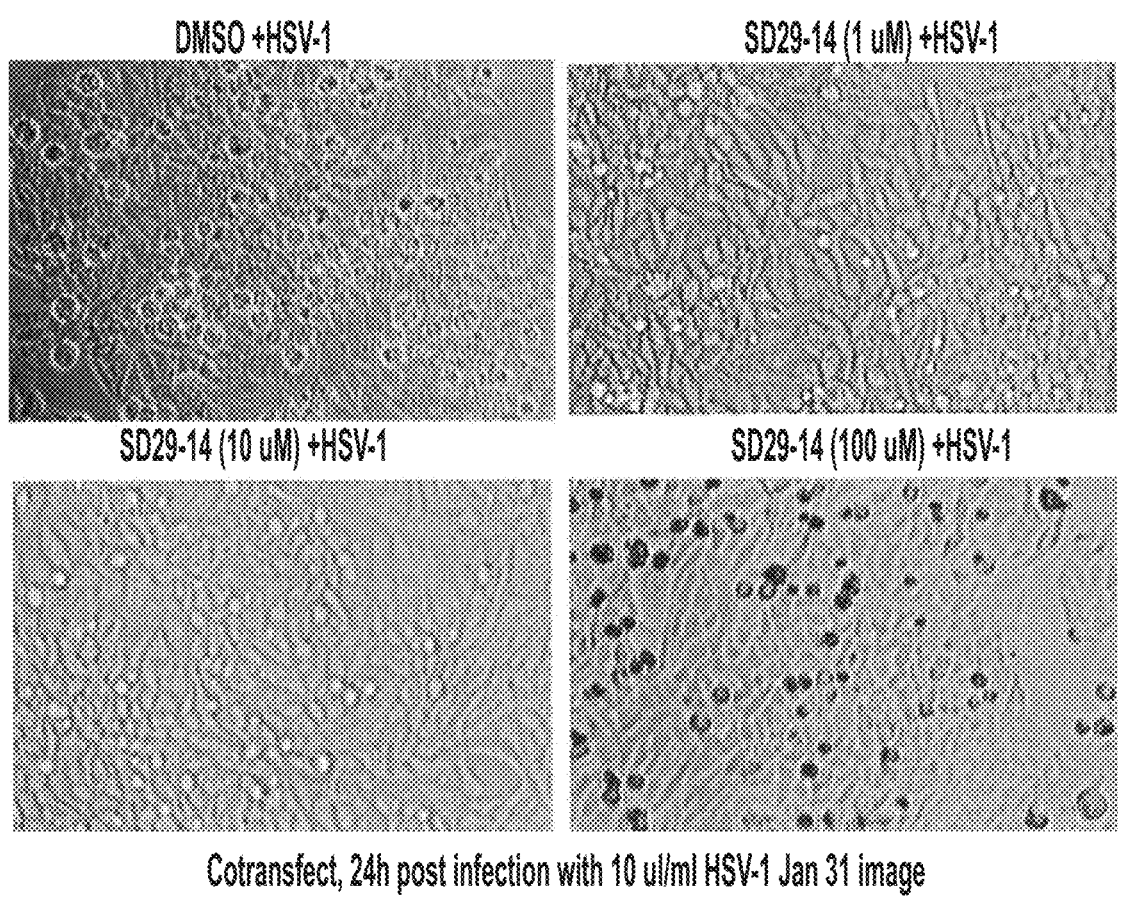
FIG. 14 shows the results where HEp-2 cells were grown to 80-90% confluency in Duibecco's Modified Eagle's medium (DMEM) supplemented with 10% fetal calf serum (PCS) and 1% penicillin-streptomycin (PS) and 1% fungicide. The HSV-1 virus and the indicated concentration of compounds were added and incubated for 24 h. After washing way the virus with PBS, image was taken under a compound microscope. The DMSO treated cells show the highest amount of cytopathic effect (round structures); while the SD29-14 at different concentrations do not show the cytopathic effect. Note that at higher concentrations of SD29-14, few cells show darker cytopathic effect but the number of those cells are significantly less than that observed with the DMSO treated cells. Cells treated with the indicated compound protected from the cytopathic effect of HSV-1 that was observed with the DMSO treatment (control).
Figure 15:
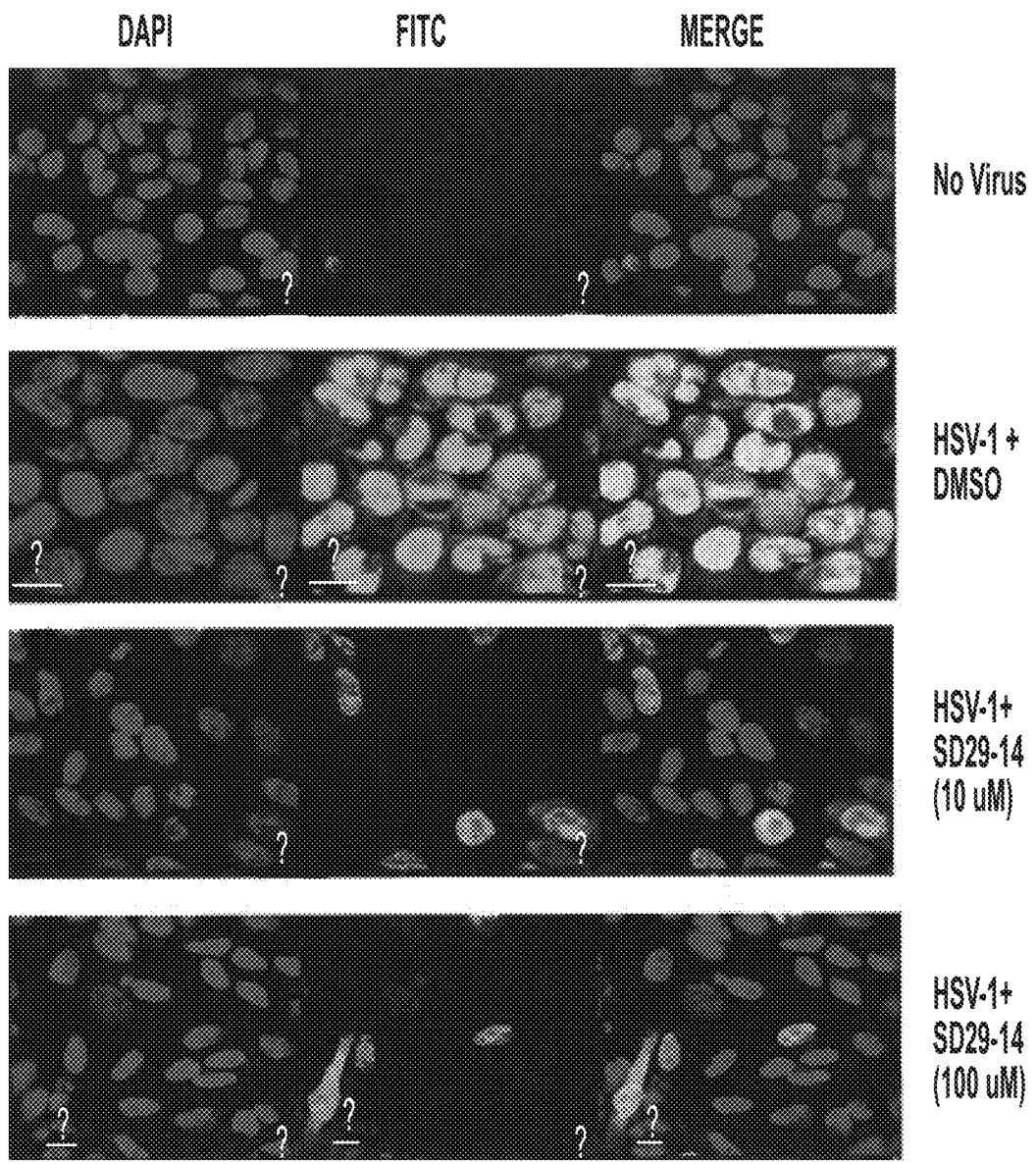
FIG. 15 shows visualization of HSV-1 proliferation inhibition by the RACK1 inhibitor compound SD29-14. The HEp-2 cells were infected with HSV-1 at an MOI of 1.0 for 30 h along with the indicated compounds and control. The cells were fixed with 4% paraformaldehyde and stained with anti-ICP0-FITC in green and DAPI (blue for DNA label in the nucleus). The slides were observed under a Nikon confocal microscope (60× magnification lens) and pictures were taken to show infected cells (green) and total cells (DAPI). All scale bars correspond to 20 µm. The imaging experiments were performed three independent times, and the results as shown are representative of one of three experiments.

Panel B of FIG. 9 shows the relative FLUC (green) and RLUC (Red) signals obtained from the cells by spectral un-mixing of the two signals. It can be seen that while DMSO treated cells produced both FLUC and RLUC signals, the drug treated cells show significant inhibition in the FLUC expression and thereby resulted in the significant inhibition in the overall IRES activity (Panel C of FIG. 9).

Though used as a positive control, the HCV IRES also showed a significant drug-induced inhibition of the IRES activities (B of FIG. 9). As the HCV can only replicate using its IRES, the inhibition of the HCV IRES by the drug(s) establishes the applicability of these drugs as anti-HCV agents as well.

Table 3 shows that the negative control constructs showed significantly low IRES activities ranging from 10-30 fold, when compared to the DMSO treated samples transfected with the dual luciferase constructs. The low IRES activities were not affected by the presence or absence of the drugs.

TABLE 3

Raw luciferase values from control construct transfections (Average Radiances)

| IRES (β-Globin) | FLUC (p/s/cm²/sr) | RLUC (p/s/cm²/sr) | FLUC/RLUC Ratio |
|---|---|---|---|
| DMSO | 5.51E+04 | 1.02E+06 | 0.055 ± 0.001 |
| SD29 (1 µM) | 4.02E+04 | 5.82E+05 | 0.068 ± 0.002 |
| SD29 (10 µM) | 3.52E+04 | 4.70E+05 | 0.074 ± 0.006 |
| SD29 (50 µM) | 3.74E+04 | 4.01E+05 | 0.093 ± 0.004 |
| SD29-14 (1 µM) | 2.21E+04 | 3.29E+09 | 0.067 ± 0.002 |
| SD29-14 (10 µM) | 2.72E+04 | 4.39E+05 | 0.062 ± 0.003 |
| SD29-14 (50 µM) | 1.74E+04 | 2.62E+05 | 0.067 ± 0.004 |

| IRES (ΔEMCV) | FLUC (p/s/cm²/sr) | RLUC (p/s/cm²/sr) | FLUC/RLUC Ratio |
|---|---|---|---|
| DMSO | 4.21E+04 | 9.68E+05 | 0.044 ± 0.005 |
| SD29 (1 µM) | 1.66E+04 | 2.49E+05 | 0.067 ± 0.002 |
| SD29 (10 µM) | 1.17E+04 | 1.36E+05 | 0.086 ± 0.003 |
| SD29 (50 µM) | 1.54E+04 | 2.25E+05 | 0.068 ± 0.003 |
| SD29-14 (1 µM) | 2.88E+04 | 4.75E+05 | 0.060 ± 0.002 |
| SD29-14 (10 µM) | 1.32E+04 | 1.90E+05 | 0.070 ± 0.000 |
| SD29-14 (50 µM) | 1.59E+04 | 2.46E+05 | 0.065 ± 0.002 |

Raw values for the FLUC and FLUC are the average radiances from three replicates. Values for the FLUC/RLUC ratio are the average of three replicates ± SEM While the subject matter disclosed herein has been described in connection with what is presently considered to be practical example embodiments, it is to be understood that the present disclosure is not limited to the disclosed embodiments, and covers various modifications and equivalent arrangements included within the spirit and scope of the appended claims.

What is claimed is:

1. A method for inhibiting the replication of a virus that utilizes an internal ribosome entry site in its replication, comprising administering a compound, a tautomer, or a pharmaceutically acceptable salt thereof, in an amount effective for inhibiting replication of the virus in cells, wherein the compound is represented by the formula:

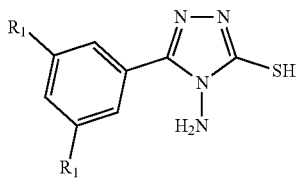

wherein each $R_1$ is independent of the other and represents a halogen atom selected from the group consisting of bromo, chloro, fluoro and iodo.

2. The method according to claim 1, wherein each $R_1$ is the same and represents bromo, chloro or fluoro.

3. The method according to claim 2, wherein each $R_1$ represents chloro.

4. The method according to claim 1, wherein the internal ribosome entry site-utilizing virus is a member of the Picornaviridae family of viruses, the Poxvirus family of viruses, or the Herpesviridae family of viruses.

5. The method according to claim 1, wherein the internal ribosome entry site-utilizing virus is an Enterovirus, HIV-1 or Hepatitis C virus.

6. The method according to claim 5, wherein the internal ribosome entry site-utilizing virus is Enterovirus D-68.

7. The method according to claim 1, wherein the internal ribosome entry site-utilizing virus is a Herpes Simplex Virus (HSV).

8. The method according to claim 7, wherein the internal ribosome entry site-utilizing virus is HSV-1.

9. A RACK1 inhibitor comprising a compound, a tautomer, or a pharmaceutically acceptable salt thereof for inhibiting replication of an internal ribosome entry site-utilizing virus in cells, wherein the compound is represented by the following formula:

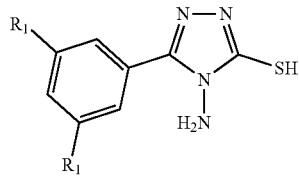

wherein each $R_1$ is independent of the other and represents a halogen atom selected from the group consisting of bromo, chloro, and iodo.

10. The RACK1 inhibitor according to claim 9, wherein the RACK1 inhibitor further comprises a carrier.

11. The RACK1 inhibitor according to claim 9, wherein each $R_1$ is the same halogen atom.

* * * * *